US011701356B2

(12) United States Patent
Withana et al.

(10) Patent No.: US 11,701,356 B2
(45) Date of Patent: Jul. 18, 2023

(54) TREATMENT OF BREAST CANCER USING COMBINATION THERAPIES COMPRISING AN AKT INHIBITOR, A TAXANE, AND A PD-L1 INHIBITOR

(71) Applicant: Genentech, Inc., South San Francisco, CA (US)

(72) Inventors: Nimali Piyushika Withana, Menlo Park, CA (US); Aruna Mani, San Carlos, CA (US); Stina Mui Singel, Menlo Park, CA (US)

(73) Assignee: GENENTECH, INC., South San Francisco, CA (US)

( * ) Notice: Subject to any disclaimer, the term of this patent is extended or adjusted under 35 U.S.C. 154(b) by 282 days.

(21) Appl. No.: 16/716,815

(22) Filed: Dec. 17, 2019

(65) Prior Publication Data
US 2020/0197396 A1 Jun. 25, 2020

Related U.S. Application Data

(60) Provisional application No. 62/822,556, filed on Mar. 22, 2019, provisional application No. 62/782,116, filed on Dec. 19, 2018.

(51) Int. Cl.
| | | |
|---|---|---|
| A61K 31/517 | (2006.01) |
| A61K 47/62 | (2017.01) |
| A61P 35/00 | (2006.01) |
| A61K 9/00 | (2006.01) |
| A61K 31/337 | (2006.01) |
| A61K 47/00 | (2006.01) |
| C07K 16/28 | (2006.01) |
| A61K 45/06 | (2006.01) |

(52) U.S. Cl.
CPC .......... *A61K 31/517* (2013.01); *A61K 9/0019* (2013.01); *A61K 31/337* (2013.01); *A61K 47/62* (2017.08); *A61P 35/00* (2018.01); *C07K 16/2827* (2013.01); *A61K 45/06* (2013.01)

(58) Field of Classification Search
CPC .... A61K 31/517; A61K 47/62; A61K 9/0019; A61K 31/337; A61K 45/06; A61P 35/00; C07K 16/2827
See application file for complete search history.

(56) References Cited

U.S. PATENT DOCUMENTS

| | | |
|---|---|---|
| 8,063,050 B2 | 11/2011 | Mitchell et al. |
| 8,853,199 B2 | 10/2014 | Mitchell et al. |
| 9,150,548 B2 | 10/2015 | Hoeflich et al. |
| 9,150,549 B2 | 10/2015 | Nannini et al. |
| 9,346,789 B2 | 5/2016 | Nannini et al. |
| 9,359,340 B1 | 6/2016 | Mitchell et al. |
| 9,610,289 B2 | 4/2017 | Nannini et al. |
| 9,682,082 B2 | 6/2017 | Lee et al. |
| 9,717,730 B2 | 8/2017 | Lin et al. |
| 10,092,567 B2 | 10/2018 | Lin et al. |

FOREIGN PATENT DOCUMENTS

| | | |
|---|---|---|
| WO | 2008006040 A1 | 1/2008 |
| WO | 2012135750 A1 | 10/2012 |
| WO | 2012135753 A1 | 10/2012 |
| WO | 2012135759 A1 | 10/2012 |
| WO | 2012135779 A1 | 10/2012 |
| WO | 2012135781 A1 | 10/2012 |
| WO | 2018/064299 A1 | 5/2018 |
| WO | 2021030248 A1 | 2/2021 |

OTHER PUBLICATIONS

Comprehensive molecular portraits of human breast tumors, Nature, Oct. 4, 2012, 490(7418):61-70 (25 pages).
Brognard et al. (May 15, 2001) "Akt/Protein Kinase B is Constitutively Active in Non-Small Cell Lung Cancer Cells and Promotes Cellular Survival and Resistance to Chemotherapy and Radiation", Cancer Research, 61:3986-3997.
Clark et al. (Jul. 2002) "Constitutive and Inducible Akt Activity Promotes Resistance to Chemotherapy, Trastuzumab, or Tamoxifen in Breast Cancer Cells", Molecular Cancer Therapeutics, 1:707-717.
Crompton et al. (Jan. 15, 2015) "Akt Inhibition Enhances Expansion of Potent Tumor-Specific Lymphocytes with Memory Cell Characteristics", Cancer Research, 75(2):296-305.
Dent et al. (2021) "Final Results Of The Double-Blind Placebo-Controlled Randomized Phase 2 LOTUS Trial Of First-Line ipatasertib Plus Paclitaxel For Inoperable Locally Advanced/Metastatic Triple-Negative Breast Cancer", Breast Cancer Research and Treatment, 189:377-386.
He et al. (Jul. 2018) "A novel PI3K/Akt-pathway activation biomarker using comprehensive genomic profiling (CGP) for clinical trial assay", Clinical Research, 78(13):3 pages.
Hurvitz et al. (Jul. 1, 2021) "Phase Ib/II Open-Label, Randomized Trial Of Atezolizumab (atezo) With Ipatasertib Kipat) And Fulvestrant (fulv) Vs Control In MORPHEUS-HR+ Breast Cancer (M-HR+ BC) And Atezo With ipat Vs Control In MORPHEUS Triple Negative Breast Cancer (M-TNBC)", San Antonio Breast Cancer Symposium, 3 pages.
Hurvitz et al. (Dec. 7-10, 2021) "Phase Ib/II Open-label, Randomized Trial of Atezolizumab With Ipatasertib and Fulvestrant vs Control in MORPHEUS-HR+ Breast Cancer and Atezolizumab With Ipatasertib vs Control in MORPHEUS Triple-Negative Breast Cancer", Abstract #21-A-434-SABCS Poster #PD10-04, 1 page.
Kim et al. (Oct. 2017) "Ipatasertib Plus Paclitaxel Versus Placebo Plus Paclitaxel As First-Line Therapy For Metastatic Triple-Negative Breast Cancer (LOTUS): A Multicentre, Randomised, Double-Blind, Placebo-Controlled, Phase 2 Trial", The Lancet Oncology, 18:1360-1372(14 pages).
Lin et al. (May 8, 2012) "An ATP-Site On-Off Switch That Restricts Phosphatase Accessibility of Akt", Science Signaling, 5(223):10 pages.

(Continued)

*Primary Examiner* — Mark Halvorson
*Assistant Examiner* — Dennis J Sullivan
(74) *Attorney, Agent, or Firm* — Mintz, Levin, Cohn, Ferris, Glovsky and Popeo, P.C.

(57) ABSTRACT

Provided herein are combination therapies comprising an AKT inhibitor, a PD-L1 antibody, and taxane for use in treating MTNBC and locally advanced TNBC.

26 Claims, 7 Drawing Sheets

(56) References Cited

OTHER PUBLICATIONS

Lin et al. (Apr. 1, 2013) "Targeting Activated Akt with GDC-0068, a Novel Selective Akt Inhibitor That Is Efficacious in Multiple Tumor Models", Clinical Cancer Research, 19(7):1760-1772 (14 pages).
Millis et al. (Dec. 2015) "Predictive Biomarker Profiling of > 6000 Breast Cancer Patients Shows Heterogeneity in TNBC, With Treatment Implications", Clinical Breast Cancer, 15(6):473-481.
Schmid et al. (Jul. 2019) "Abstract CT049: Phase Ib study evaluating a triplet combination of ipatasertib (IPAT), atezolizumab (atezo), and paclitaxel (PAC) or nab-PAC as first-line (1 L) therapy for locally advanced/metastatic triplenegative breast cancer (TNBC)", Cancer Research, 4 pages.
Schmid et al. (2021) "Abstract PD14-03: Molecular Mechanism Of Ipatasertib (IPAT)And Its Combination With Atezolizumab (atezo) In Patients(pts) With Locally Advanced/Metastatic Triple-Negative Breastcancer (aTNBC)", Cancer Research, 81(4_Supplement): 4 pages.
Schmid et al. (2021) "Abstract PS12-28: Phase 1b Study Evaluating A Triplet Combination Of Ipatasertib (IPAT), Atezolizumab, And A Taxane As First-Line Therapy For Locally Advanced/Metastatic Triple-Negative Breast Cancer (TNBC)", Cancer Research, 81 (4_Supplement): PS12-28 (4 pages).
Schmid et al. (Oct. 20, 2018) "Atezolizumab and Nab-Paclitaxel in Advanced Triple-Negative Breast Cancer", Th New England journal of Medicine, 379(22):2108-2121.
Schmid et al. (2018) "AZD5363 Plus Paclitaxel Versus Placebo Plus Paclitaxel As First-Line Therapy For Metastatic Triple-Negative Breast Cancer (PAKT): A Randomised, Double Blind, Placebo-Controlled, Phase II Trial", Journal of Clinical Oncology, 36(15): 5 pages.
Schmid et al. (2021) "Barbican: A randomized, phase II study to determine the contribution of ipatasertib to neoadjuvant chemotherapy plus atezolizumab in women with triple-negative breast cancer", Annals of Oncology, 32 (S5);S411-S412.
Schmid et al. (Dec. 8-11, 2020) "Molecular mechanism of ipatasertib and its combination with atezolizumab in patients with locally advanced/metastatic triple-negative breast cancer", San Antonio Breast Cancer Symposium, Poster No. PD14-03, 1 page.
Schmid et al. (Jun. 24, 2020) "Phase 1b Study Evaluating A Triplet Combination Of Ipatasertib (IPAT), Atezolizumab (Atezo), And Paclitaxel (PAC) Or Nab-PAC As First-Line (1L) Therapy For Locallyadvanced/Metastatic Triple-Negative Breast Cancer (aTNBC)", Available on https://www.abstractserver.com/seno2020/uploads/24-COI-1580986578.pdf, 17 (02):e26-e27.
Schmid et al. (Dec. 8-11, 2020) "Phase 1b study evaluating a triplet combination of ipatasertib, atezolizumab, and a taxane as first-line therapy for locally advanced/metastatic triple-negative breast cancer", San Antonio Breast Cancer Symposium, Poster No. PS12-28, 1 page.
Schmid et al. (Mar. 29-Apr. 3, 2019) "Phase 1b Study Evaluating A Triplet Combination Of Ipatasertib, Atezolizumab, And Paclitaxel Or Nab-Paclitaxel As First-Line Therapy For Locally Advanced/Metastatic Triple-Negative Breast Cancer", Presented at the American Association for Cancer Research Annual Meeting, 1 page.
Solit et al. (May 1, 2003) "Inhibition of Heat Shock Protein 90 Function Down-Regulates Akt Kinase and Sensitizes Tumors to Taxol", Cancer Research, 63: 2139-2144 (7 pages).
Wallin et al. (Sep. 8, 2010) "Nuclear Phospho-Akt Increase Predicts Synergy of PI3K Inhibition and Doxorubicin in Breast and Ovarian Cancer", Science Translational Medicine, 2(48):48ra66 (9 pages).
Xu et al. (Mar. 15, 2012) "Akt: A Double-Edged Sword in Cell Proliferation and Genome Stability", Journal of Oncology, 2012:15 pages.
Xue et al. (Jun. 11, 2015) "Integrated Akt/PKB Signaling in Immunomodulation and Its Potential Role in Cancer Immunotherapy", Journal of the National Cancer Institute, 107(7):djv171 (10 pages).
Yan et al. (Dec. 15, 2013) "Evaluation and Clinical Analyses of Downstream Targets of the Akt Inhibitor GDC-0068", Clinical Cancer Research, 19(24):6976-6986.
Yang et al. (Apr. 2016) "New insights on PI3K/AKT pathway alterations and clinical outcomes in breast cancer", Cancer Treatment Reviews, 45:87-96 (20 pages).
Adams, S., et al., "Phase Ib trial of atezolizumab in combination with nab-paclitaxel in patients with metastatic triple-negative breast cancer (mTNBC)" J Clin Oncol 34(15 Suppl 1009):1-2 (May 26, 2016).
Diana, A., et al., "Triple Negative Brease Cancers: Systematic Review of the Literature on Molecular and Clinical Features with a Focus on Treatment with Innovative Drugs" Curr Oncology Reports 20(10):1-11 (Aug. 20, 2018).
F. Hoffmann-LaRoche AG et al., "HY 2017 Results" F. Hoffmann-LaRoche AG:1-3, 98-99, 119 (Jul. 27, 2017) https://www.roche.com/dam/jcr:35ee4c5e-cb3d-49a5-9893-78d9757cef02/en/irp170727.pdf.
"International Search Report—PCT/US2019/066684" (w/Written Opinion),:pp. 1-12 (dated Apr. 15, 2020).

TREATMENT OF BREAST CANCER USING COMBINATION THERAPIES COMPRISING AN AKT INHIBITOR, A TAXANE, AND A PD-L1 INHIBITOR

CROSS REFERENCE TO RELATED APPLICATIONS

This non-provisional patent application claims the benefit of U.S. Provisional Patent Application No. 62/782,116, filed Dec. 19, 2018, and U.S. Provisional Patent Application No. 62/822,556, filed Mar. 22, 2019, each of which is incorporated herein by reference in its entirety and for all purposes.

FIELD OF THE INVENTION

Provided herein are combination therapies comprising an AKT inhibitor (e.g. ipatasertib); a taxane (e.g. paclitaxel or nab-paclitaxel); and a PD-L1 therapeutic antibody (e.g. atezolizumab) for the treatment of breast cancers.

BACKGROUND

Globally, breast cancer is the second most common invasive malignancy and the most common cause of cancer-related mortality in women, with a 5-year survival rate following metastatic diagnosis of approximately 15% (Jemal et al. 2011; Ferlay et al. 2015).

Triple-negative breast cancer (TNBC) accounts for approximately 20% of all breast cancers and is defined by the absence of immunostaining for estrogen receptor (ER), progesterone receptor (PgR), and non-amplified HER2 expression (per American Society of Clinical Oncology [ASCO]/College of American Pathologists [CAP] guidelines [ASCO-CAP 2010; 2013, 2018]). Patients with metastatic TNBC (MTNBC) exhibit a particularly poor clinical outcome, generally with rapid progression and a median overall survival (OS) rate of approximately 16 months (Rodler et al. 2010; Miles et al. 2013). There are no currently approved first-line regimens or targeted therapies for patients with this specific subtype of breast cancer.

MBC remains an incurable disease. For patients with MTNBC, clinical outcome is particularly poor, generally with rapid progression and a median OS of approximately 16 months (Rodler et al. 2010; Miles et al. 2013). Although chemotherapy is a mainstay treatment, resistance inevitably develops and benefit is often short-lived.

Accordingly, there is a pressing need for clinically active agents for treatment of MTNBC.

SUMMARY

Provided herein are solutions to the problems above and other problems in the art.

In a first aspect provided herein is a combination therapy comprising ipatasertib, atezolizumab, and paclitaxel. In a second aspect provided herein is a combination therapy comprising ipatasertib, atezolizumab, and nab-paclitaxel.

In a third aspect provided herein are methods of treating metastatic triple negative breast cancer (MTNBC) and locally advanced TNBC by administering a combination therapy comprising ipatasertib, atezolizumab, and a taxane (e.g. paclitaxel or nab-paclitaxel).

In another aspect provided herein is a method of treating MTNBC by administering a combination therapy comprising a dosing regimen as set forth in method M1 (e.g. a combination therapy comprising ipatasertib, atezolizumab, and paclitaxel) as provided herein. In another aspect provided herein is a method of treating MTNBC by administering a combination therapy comprising a dosing regimen as set forth in method M2 (e.g. a combination therapy comprising ipatasertib, atezolizumab, and nab-paclitaxel) provided herein.

In still another aspect provided herein is a method of treating MTNBC by administering a combination therapy comprising a dosing regimen as set forth in method M3 (e.g. a combination therapy comprising ipatasertib, atezolizumab, and paclitaxel) as provided herein. In still another aspect provided herein is a method of treating MTNBC by administering a combination therapy comprising a dosing regimen as set forth in method M4 (e.g. a combination therapy comprising ipatasertib, atezolizumab, and paclitaxel) as provided herein.

In yet another aspect provided herein is a method of treating MTNBC by administering a combination therapy comprising a dosing regimen as set forth in method M5 (e.g. a combination therapy comprising ipatasertib, atezolizumab, and paclitaxel) as provided herein. In another aspect provided herein is a method of treating MTNBC by administering a combination therapy comprising a dosing regimen as set forth in method M6 (e.g. a combination therapy comprising ipatasertib, atezolizumab, and paclitaxel) as provided herein.

In another aspect provided herein is a method of treating locally advanced TNBC by administering a combination therapy comprising a dosing regimen as set forth in method L1 (e.g. a combination therapy comprising ipatasertib, atezolizumab, and paclitaxel) as provided herein. In another aspect provided herein is a method of treating locally advanced TNBC by administering a combination therapy comprising a dosing regimen as set forth in method L2 (e.g. a combination therapy comprising ipatasertib, atezolizumab, and nab-paclitaxel) provided herein.

In still another aspect provided herein is a method of treating locally advanced TNBC by administering a combination therapy comprising a dosing regimen as set forth in method L3 (e.g. a combination therapy comprising ipatasertib, atezolizumab, and paclitaxel) as provided herein. In still another aspect provided herein is a method of treating locally advanced TNBC by administering a combination therapy comprising a dosing regimen as set forth in method L4 (e.g. a combination therapy comprising ipatasertib, atezolizumab, and paclitaxel) as provided herein.

In yet another aspect provided herein is a method of treating locally advanced TNBC by administering a combination therapy comprising a dosing regimen as set forth in method L5 (e.g. a combination therapy comprising ipatasertib, atezolizumab, and paclitaxel) as provided herein. In another aspect provided herein is a method of treating locally advanced TNBC by administering a combination therapy comprising a dosing regimen as set forth in method L6 (e.g. a combination therapy comprising ipatasertib, atezolizumab, and paclitaxel) as provided herein.

In another aspect provided herein is a method of inhibiting tumor growth or producing/increasing tumor regression in a patient having MTNBC or locally advanced TNBC by administering to the patient a combination therapy described herein according to the methods described herein.

In some embodiments, the cancer cells in the patient express PD-L1. In some embodiments, the expression of PD-L1 may be determined by an immunohistochemistry (IHC) assay. In some embodiments, the cancer cells in a patient have a phosphatase and tensin homolog (PTEN) mutation, loss of PTEN expression, a phosphatidylinositol- 4,5-bisphosphate 3-kinase catalytic subunit alpha (PIK3CA) mutation, a protein kinase B alpha (AKT1) mutation, or a combination thereof, where such mutation can be determined using NGS.

The present embodiments can be understood more fully by reference to the detailed description and examples, which are intended to exemplify non-limiting embodiments.

DETAILED DESCRIPTION

Figure 1:
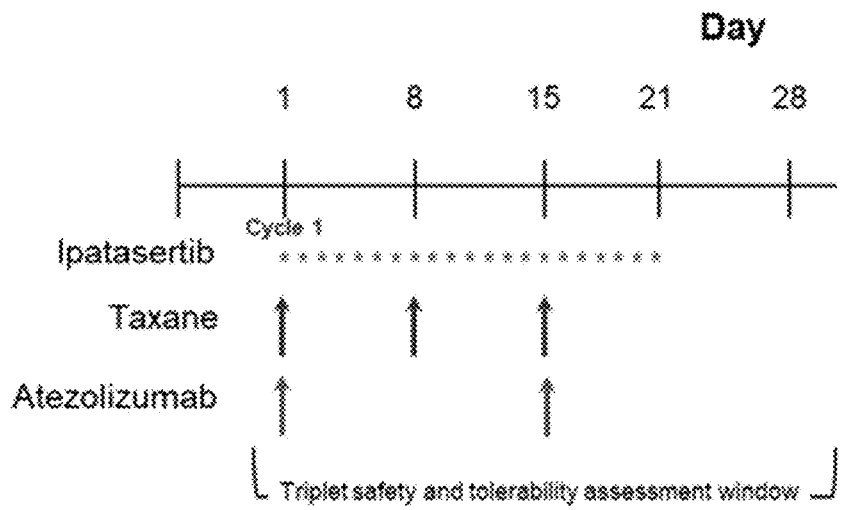
FIG. 1 depicts administration of a combination therapy described herein where ipatasertib is administered on C1D1 and consecutively for 21 days followed by a 7-day rest period. A taxane (e.g. paclitaxel or nab-paclitaxel as described herein) is administered on Days 1, 8, and 15 of the 28-day cycle. Atezolizumab is administered on Days 1 and 15 of the cycle.
Figure 2:
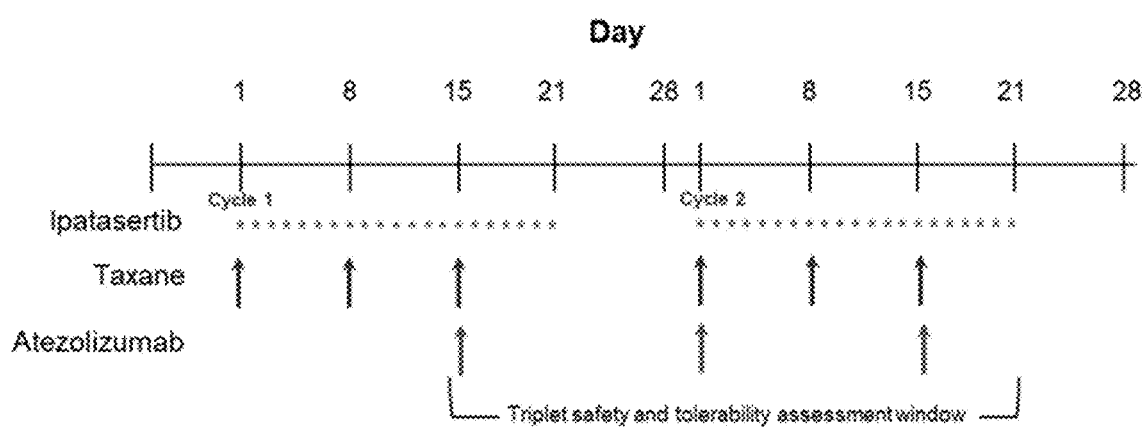
FIG. 2 depicts administration of a combination therapy described herein where ipatasertib is administered on C1D1 and consecutively for 21 days followed by a 7-day rest period. A taxane (e.g. paclitaxel or nab-paclitaxel as described herein) is administered on Days 1, 8, and 15 of the cycle. Atezolizumab is administered on Day 15 of the first cycle and on Days 1 and 15 of each cycle thereafter.
Figure 3:
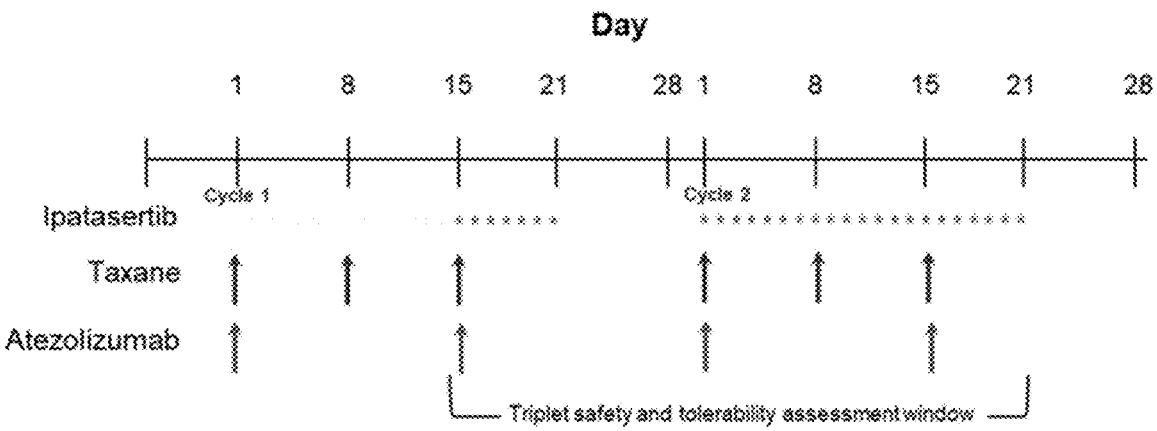
FIG. 3 depicts administration of a combination therapy described herein where a taxane (e.g. paclitaxel or nab-paclitaxel as described herein) is administered on Days 1, 8, and 15 of the first cycle. Atezolizumab is administered on Days 1 and 15 of the first cycle. Ipatasertib is administered QD on Days 15-21 of the first cycle followed by a 7-day rest period and then administered starting of D1 of the next cycle for 21 consecutive days.

Unless defined otherwise, all technical and scientific terms used herein have the same meaning as commonly understood by one of ordinary skill in the art to which the invention belongs. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

"Ipatasertib" refers to a compound having the structure:

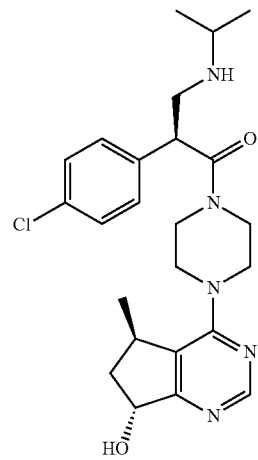 [SMILES: CC(C)NC[C@@H](C(=O)N1CCN(c2ncnc3c2[C@H](C)C[C@H]3O)CC1)c1ccc(Cl)cc1]

having the chemical name (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one. In one embodiment, ipatasertib is a monohydrochloride salt. In one embodiment, ipatasertib is an amorphous monohydrochloride salt.

"Atezolizumab" refers to a programmed cell death ligand 1 (PD-L1) blocking antibody. Atezolizumab is marketed in the US under the tradename TECENTRIQ®. Atezolizumab is an Fc-engineered, humanized, non-glycosylated IgG1 kappa immunoglobulin that has a calculated molecular mass of 145 kDa. Atezolizumab is a monoclonal antibody that binds to PD-L1 and blocks its interactions with both PD-1 and B7.1 receptors. This releases the PD-L1/PD-1 mediated inhibition of the immune response, including activation of the anti-tumor immune response without inducing antibody dependent cellular cytotoxicity.

"Paclitaxel" refers to a compound having the structure:

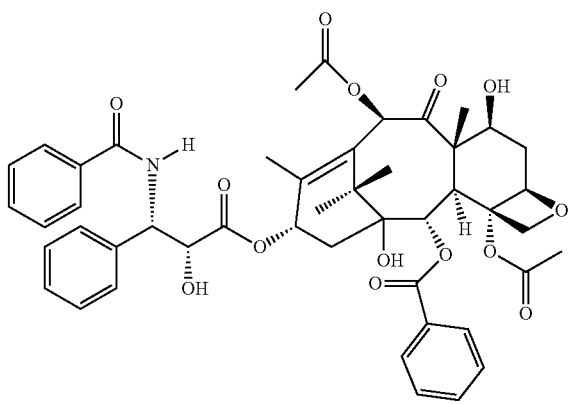

having the chemical name (2aR,4S,4aS,6R,9S,11 S,12S, 12aR,12bS)-1,2a,3,4,4a,6,9,10,11,12,12a,12b-Dodecahydro-4,6,9,11,12,-12b-hexahydroxy-4a,8,13,13-tetramethyl-7, 11-methano-5H-cyclodeca [3,4] benz [1,2-b] oxet-5-one 6,12b-diacetate, 12-benzoate, 9-ester with (2R,3S)—N-benzoyl-3-phenylisoserine and also known as 5β,20-Epoxy1, 2α,4,7β,10β,13α-hexahydroxytax-11-en-9-one 4,10-diacetate 2-benzoate 13-ester with (2R,3S)—N-benzoyl-3-phenylisoserine. In one embodiment, paclitaxel is marketed in the U.S. under the tradename TAXOL®.

"Nab-paclitaxel" refers to an injectable suspension comprising paclitaxel protein-bound particles (albumin bound). Nab-paclitaxel is formulated as albumin-bound nanoparticles with a mean particle size of approximately 130 nanometers. Paclitaxel exists in the particles in a non-crystalline, amorphous state. Nab-paclitaxel is marketed in the U.S. under the tradename ABRAXANE®. Nab-paclitaxel can be supplied as a lyophilized powder for reconstitution in, for example, 20 mL of 0.9% Sodium Chloride Injection, USP prior to intravenous infusion.

"Triple Negative Breast Cancer" or "TNBC" refers to breast cancer characterized by decreased or no expression of estrogen receptor (ER-negative), progesterone receptor (PR-negative), and human epidermal growth factor receptor 2 (HER2-negative). The term is well understood by those in the art. Current standard of care for triple negative breast cancer (TNBC), is determined by both disease (stage, pace of disease, etc.) and patient (age, co-morbidities, symptoms, etc.) characteristics.

"Metastatic Triple Negative Breast Cancer" or "MTNBC refers to cancer that has spread to tissues beyond the local breast tissue and regional lymph nodes. "Locally Advanced Triple Breast Cancer" or "Locally advanced TNBC" refers to cancer that has spread from the breast tissue only to surrounding tissue.

"Overall survival" or "OS" refers to the time from enrollment to death from any cause.

"Objective response rate" or "ORR" refers the proportion of patients with a confirmed complete response or partial response on two consecutive occasions ≥4 weeks apart, as determined by the investigator according to RECIST v1.1

"Time to progression" or "TTP" refers to the time from randomization until objective tumor progression.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

"Clinical benefit rate" or "CBR" refers to the proportion of patients with stable disease for at least 24 weeks or with confirmed complete or partial response, as determined by the investigator according to RECIST v1.1.

"Complete response" or "CR" refers to the disappearance of all target lesions and non-target lesions and (if applicable) normalization of tumor marker level.

"Partial response" or "non-CR/Non-PD" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

"Progressive disease" or "PD" refers to ≥20% increase in sum of diameters of target lesions, unequivocal progression in non-target lesions, and/or appearance of new lesions.

"Stable disease" or "SD" refers to neither sufficient shrinkage to qualify for CR or PR nor sufficient increase growth of tumor to qualify for PD.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a breast cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a breast cancer described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement or prevention of a breast cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. Thus, an "effective amount" may be considered in the context of administering one or more therapeutic agents, and a single agent may be considered to be given in an effective amount if, in conjunction with one or more other agents, a desirable result may be or is achieved.

An "administration period" or "cycle" refers to a period of time comprising administration of one or more agents described herein (i.e. ipatasertib, atezolizumab, paclitaxel, and nab-paclitaxel) and an optional period of time comprising no administration of one or more of the agents described herein. For example, a cycle can be 28 days in total length and include administration of one or more agents for 21 days and a rest period of 7 days. A "rest period" refers to a period of time where at least one of the agents described herein (e.g. ipatasertib, atezolizumab, paclitaxel, and nab-paclitaxel) are not administered. In one embodiment, a rest period refers to a period of time where none of the agents described herein (e.g. ipatasertib, atezolizumab, paclitaxel, and nab-paclitaxel) are administered. A rest period as provided herein can in some instances include administration of another agent that is not ipatasertib, atezolizumab, paclitaxel, or nab-paclitaxel. In such instances, administration of another agent during a rest period should not interfere or detriment administration of an agent described herein.

A "dosing regimen" refers to a period of administration of the agents described herein comprising one or more cycles, where each cycle can include administration of the agents described herein at different times or in different amounts.

"QD" refers to administration of a compound once daily.

A graded adverse event refers to the severity grading scale as established for by NCI CTCAE. In one embodiment, the adverse event is graded in accordance with the table below.

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living [a] |
| 3 | Severe or medically significant, but not immediately life-threatening; hospitalization or prolongation of hospitalization indicated; disabling; or limiting self-care activities of daily living [b, c] |
| 4 | Life-threatening consequences or urgent intervention indicated [d] |
| 5 | Death related to adverse event [d] |

Combination Therapies

Provided herein are combination therapies comprising an ATP competitive AKT inhibitor, a PD-L1 antibody, and a taxane. In one embodiment is a combination therapy comprising ipatasertib, atezolizumab, and a taxane. In one embodiment, a taxane as used herein refers to paclitaxel or nab-paclitaxel. In another embodiment is a combination therapy comprising ipatasertib, atezolizumab, and paclitaxel. In another embodiment, is a combination therapy comprising ipatasertib, atezolizumab, and nab-paclitaxel.

The combination therapies described herein can be provided as a kit comprising one or more of the agents for administration. In one embodiment, the kit includes ipatasertib and atezolizumab. In another embodiment, the kit includes ipatasertib, atezolizumab, and either paclitaxel or nab-paclitaxel. In one embodiment, the agents of the combination therapy described herein are supplied in a kit in a form ready for administration or, for example, for reconstitution (e.g. for IV administration as described herein). Kits described herein can include instructions such as package inserts. In one embodiment, the instructions are package inserts—one for each agent in the kit.

Methods of Treating

Provided herein are methods of treating triple negative breast cancer (TNBC), particularly metastatic (MTNBC) and locally advanced TNBC. In one embodiment, the method includes treating MTNBC in a patient having MTNBC by administering to the patient a combination therapy that includes ipatasertib, atezolizumab, and a taxane such as paclitaxel or nab-paclitaxel. In another embodiment is a method of treating locally advanced TNBC in a patient having locally advanced TNBC by administering to the patient a combination therapy that includes ipatasertib, atezolizumab, and a taxane such as paclitaxel or nab-paclitaxel.

Despite multiple treatment options, advanced breast cancer, such as MTNBC and locally advanced TNBC, remains an incurable disease. Although chemotherapy is a mainstay treatment for TNBC, resistance often develops and benefit is often short lived. Ipatasertib administered with paclitaxel appears to show clinical benefit for TNBC as demonstrated in completed and ongoing clinical studies. In addition, cancer immunotherapies (CIT), such as anti-PD-L1 antibodies like atezolizumab, have shown clinical benefit in the treatment of TNBC (Nanda R, et al. J Clin Oncol 2016; 34:2460-7; Schmid P, et al. AACR 108th Annual Meeting, Apr. 1-5, 2017; abstract 2986). However, even in view of these studies, TNBC can progress after treatment, facilitating the need for new and innovative treatment strategies.

Taxanes, including paclitaxel, are increasingly used for adjuvant treatment of HER2-negative breast cancers worldwide. Many patients receive adjuvant chemotherapy, including taxanes, which can cause concern about rechallenge with taxane treatment at recurrence when patients first relapse in the advanced setting. Nab-paclitaxel is an albumin-bound formulation of paclitaxel that was developed to mitigate the significant toxicities associated with the vehicles that are necessary for parenteral administration of sb-paclitaxel (e.g. polyethylated castor oil and polysorbate 80). In addition, it has an advantageous PK profile compared with sb-paclitaxel and achieves a 33% higher tumor uptake in preclinical models. (Yardley D A. J Control Release 2013; 170:365-72.) Steroids can be administered with sb-paclitaxel to lower the risk of hypersensitivity allergic reactions, but steroid premedication is not required with the use of nab-paclitaxel.

In breast cancer, Akt appears to be one node along the PI3K/Akt pathway that controls apoptosis and cell growth (Yap T A, et al. Curr Opin Pharmacol 2008; 8:393-412), and this pathway is known to be activated in breast cancers. Up-regulation of Akt signaling (whether intrinsic or induced following chemotherapy) represents one potential survival pathway in response to genotoxic or mitotic stress. (Xu N, et al. J Oncol 2012; 2012:951724. doi: 10.1155/2012/951724.)

One available CIT approach is to circumvent immune evasion mechanisms and reinvigorate anti-tumor responses by identifying and targeting T-cell co-inhibitory surface receptors such as CTLA-4 and PD-L1/PD-1. While these targets have resulted in varied clinical therapeutic success for, ongoing research indicates a series of stepwise events is necessary for the generation of a continuous anti-tumor immune response. (Chen D S, Mellman I. Immunity 2013; 39:1-10). Each event appears useful for an effective response, and each is also susceptible to several tumor immune evasion mechanisms.

The PD-L1 pathway serves as an immune checkpoint to temporarily dampen immune responses in states of chronic antigen stimulation, such as chronic infection or cancer. PD-L1 is an extracellular protein that down-regulates immune responses through binding to its two receptors, PD-1 and B7-1. PD-1 is an inhibitory receptor expressed on T cells following T-cell activation, and expression is sustained in states of chronic stimulation. (Blank C, et al. Cancer Immunol Immunother 2005; 54:307-14; Keir M E, et al. Annual Rev Immunol 2008; 26:677-704.) B7-1 is a molecule expressed on antigen-presenting cells and activated T cells. Binding of PD-L1 to PD-1 and B7-1 inhibits T-cell proliferation and activation, cytokine production, and cytolytic activity, leading to the functional inactivation or exhaustion of T cells. (Butte M J, et al. Immunity 2007; 27:111-22; Yang J, et al. J Immunol 2011; 187:1113-9). Overexpression of PD-L1 on tumor cells has been reported to impede anti-tumor immunity, resulting in immune evasion. (Blank C, et al. Cancer Immunol Immunother 2007; 56:739-45.)

Targeting the PD-L1 pathway with atezolizumab has demonstrated activity in patients with advanced malignancies who had progression of disease with standard-of-care therapies. Objective responses have been observed in a broad range of malignancies, including NSCLC, urothelial carcinoma, renal cell carcinoma, melanoma, colorectal cancer, head and neck cancer, gastric cancer, breast cancer, and sarcoma. The combination of atezolizumab and nab-paclitaxel has shown encouraging efficacy (Adams S, et al. J Clin Oncol 2016; 34(suppl; abstr 1009).)

In one aspect provided herein is a method of treating metastatic triple negative breast cancer (MTNBC) in a patient having MTNBC by administering to the patient a combination therapy comprising (i) ipatasertib; (ii) atezolizumab; and (iii) paclitaxel or nab-paclitaxel, where the combination therapy is administered over a 28-day cycle. In one embodiment, the method includes a combination therapy comprising (i) ipatasertib; (ii) atezolizumab; and (iii) paclitaxel. In one embodiment, the method includes a combination therapy comprising (i) ipatasertib; (ii) atezolizumab; and (iii) nab-paclitaxel.

Agents described herein can be administered in accordance with a package insert. In one embodiment of the methods described herein, agents can be administered in an effective amount as described herein. In one embodiment of the methods described herein, ipatasertib is administered at an amount of 400 mg. Such administration can be in a single dose (i.e. a single or multiple pills). In one embodiment, the dose of ipatasertib is reduced to 300 mg or 200 mg when a patient described herein experiences an adverse event associated with treatment with ipatasertib or where, for example, the dose of ipatasertib is otherwise not tolerated by the patient during treatment. Ipatasertib can be administered QD as described herein.

In one embodiment of the methods described herein, administration of ipatasertib occurs before IV infusion of another agent (e.g. atezolizumab, paclitaxel or nab-paclitaxel). In one embodiment of the methods described herein, administration of ipatasertib occurs before administration of atezolizumab and the administration of atezolizumab occurs before the administration of paclitaxel or nab-paclitaxel.

In one embodiment, patients are tested for the presence, level, or amount of a compound having structure:

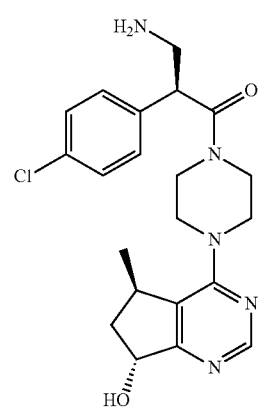 [SMILES: C[C@@H]1C[C@@H](O)c2ncnc(N3CCN(C(=O)[C@H](CN)c4ccc(Cl)cc4)CC3)c21]

having the chemical name, (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one, which is a metabolite of ipatasertib.

In another embodiment of the methods described herein, atezolizumab is administered at a dose of about 700 mg to about 900 mg every two weeks (Q2W) (e.g., about 750 mg to about 900 mg every two weeks, e.g., about 800 mg to about 850 mg every two weeks). In one embodiment of the methods described herein, atezolizumab is administered in accordance with a package insert.

In one embodiment of the methods described herein, atezolizumab is administrated at an amount of 840 mg by intravenous (IV) infusion. In one embodiment of the methods described herein, the first administration of atezolizumab is infused over 60 (±15) min. In one embodiment of the methods described herein, subsequent administrations of atezolizumab as described herein are performed over 30 (±10) min. In one embodiment of the methods described herein, atezolizumab is administered at an amount of 840 mg Q2W.

In another embodiment of the methods described herein, atezolizumab is administered in accordance with a package insert.

In one embodiment of the methods described herein, paclitaxel is administered as an agent of the triple combination therapy described herein at an amount of 80 mg/m$^2$ by IV infusion. In one embodiment of the methods described herein, the dose of paclitaxel is reduced to 65 mg/m$^2$ when a patient described herein experiences an adverse event associated with treatment with paclitaxel or where, for example, the dose of paclitaxel is otherwise not tolerated by the patient during treatment. In one embodiment of the methods described herein, paclitaxel is administered over 60 minutes for each administration. In another embodiment of the methods described herein, paclitaxel is administered in accordance with a package insert.

In one embodiment of the methods described herein, a patient described herein must be premedicated prior to administration of paclitaxel as set forth herein with dexamethasone, diphenhydramine, and an H2 receptor blocker (i.e., ranitidine or famotidine). In one embodiment of the methods described herein, the H2 receptor antagonist is not cimetidine or a H2 receptor agonist known to inhibit cytochrome P450.

In one embodiment of the methods described herein, nab-paclitaxel is administered as an agent of the triple combination therapy described herein at an amount of 100 mg/m$^2$ by IV infusion. In one embodiment of the methods described herein, the dose of nab-paclitaxel is reduced to 75 mg/m$^2$ or 50 mg/m$^2$ when a patient described herein experiences an adverse event associated with treatment with nab-paclitaxel or where, for example, the dose of nab-paclitaxel is otherwise not tolerated by the patient during treatment. In one embodiment of the methods described herein, nab-paclitaxel is administered over 30 minutes for each administration. In another embodiment of the methods described herein, nab-paclitaxel is administered in accordance with a package insert.

In one embodiment of the methods described herein, atezolizumab administration is suspended for 3-12 weeks where a patient described herein experiences an adverse event related to atezolizumab. In one embodiment of the methods described herein, ipatasertib administration is suspended for 1-28 days where a patient described herein experiences an adverse event related to ipatasertib. In one embodiment of the methods described herein, the study cycle day count does not reset if an agent described herein is suspended during the cycle.

In one embodiment, the methods described herein include a combination therapy described herein administered according to a dosing regimen comprising one 28-day cycle. In another embodiment, the methods described herein include a combination therapy described herein administered according to a dosing regimen comprising a first 28-day cycle followed by 2-36 28-day cycles. In still another embodiment, the methods described herein include a combination therapy described herein administered according to a dosing regimen comprising a first 28-day cycle followed by 2-24 28-day cycles. In one embodiment of the methods described herein, the dosing regimen comprises a first 28-day cycle followed by 2-36, 2-30, 2-24, 2-20, 2-16, 2-14, 2-12, 2-10, 2-8, 2-6, 2-5, or 2-4 28-day cycles. In another embodiment of the methods described herein, the dosing regimen comprises a first 28-day cycle followed by 2, 3, 4, 5, 6, 7, 8, 9, or 10 28-day cycles. In still another embodiment of the methods described herein, the dosing regimen comprises a first 28-day cycle followed by at least 2, 3, 4, 5, 6, 7, 8, 9, 10, 12, 14, or 16 28-day cycles.

Further embodiments of the methods of treating MTNBC and locally advanced TNBC are provided herein.

In one embodiment, provided herein is a first method of treating MTNBC ("M1") in a patient having MTNBC by administering a combination therapy as described herein to the patient where the combination therapy is administered according to a dosing regimen comprising:
(i) administration of ipatasertib QD on day 1 through day 21;
(ii) administration of atezolizumab on day 1 and day 15;
(iii) administration of paclitaxel on day 1, day 8, and day 15; and
(iv) a rest period of at least 7 days.

In one embodiment of the first method (M1) of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the first method (M1) of treating MTNBC, the patient is administered at least 5 or at least 10 cycles of the dosing regimen.

In another embodiment provided herein is a second method of treating MTNBC ("M2") in a patient having MTNBC by administering a combination therapy as described herein to the patient where the combination therapy is administered according to a dosing regimen comprising:
(i) administration of ipatasertib QD on day 1 through day 21;
(ii) administration of atezolizumab on day 1 and day 15;
(iii) administration of nab-paclitaxel on day 1, day 8, and day 15; and
(iv) a rest period of at least 7 days.

In one embodiment of the second method (M2) of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the second method (M2) of treating MTNBC, the patient is administered at least 5 or at least 10 cycles of the dosing regimen.

In another embodiment provided herein is a third method of treating MTNBC ("M3") in a patient having MTNBC by administering a combination therapy as described herein to the patient where the combination therapy is administered according to a dosing regimen comprising:
(i) administration of ipatasertib QD on day 1 through day 21;
(ii) administration of atezolizumab on day 15;
(iii) administration of paclitaxel on day 1, day 8, and day 15; and
(iv) a rest period of at least 7 days.

In one embodiment of the third method (M3) of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the third method (M3) of treating MTNBC, the patient is administered at least 5 or at least 10 cycles of the dosing regimen.

In still another embodiment provided herein is a fourth method of treating MTNBC ("M4") in a patient having MTNBC by administering a combination therapy as described herein to the patient where the combination therapy is administered according to a dosing regimen comprising:
(i) administration of ipatasertib QD on day 1 through day 21;
(ii) administration of atezolizumab on day 15;
(iii) administration of nab-paclitaxel on day 1, day 8, and day 15; and
(iv) a rest period of at least 7 days.

In one embodiment of the fourth method (M4) of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the fourth method (M4) of treating MTNBC, the patient is administered at least 5 or at least 10 cycles of the dosing regimen.

In still another embodiment provided herein is a fifth method of treating MTNBC ("M5") in a patient having MTNBC by administering a combination therapy as described herein to the patient where the combination therapy is administered according to a dosing regimen comprising:
(i) administration of atezolizumab on day 1 and day 15;
(ii) administration of paclitaxel on day 1, day 8, and day 15;
(iii) administration of ipatasertib QD on day 15 through day 21; and
(iv) a rest period of at least 7 days.

In one embodiment of the fifth method (M5) of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the fifth method (M5) of treating MTNBC, the patient is administered at least 5 or at least 10 cycles of the dosing regimen.

In yet another embodiment provided herein is a sixth method of treating MTNBC ("M6") in a patient having MTNBC by administering a combination therapy as described herein to the patient where the combination therapy is administered according to a dosing regimen comprising:
(i) administration of atezolizumab on day 1 and day 15;
(ii) administration of nab-paclitaxel on day 1, day 8, and day 15;
(iii) administration of ipatasertib QD on day 15 through day 21; and
(iv) a rest period of at least 7 days.

In one embodiment of the sixth method of treating MTNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the sixth method (M6) of treating MTNBC, the patient is administered at least 5 or at least 10 cycles of the dosing regimen.

Also provided herein is a first method of treating locally advanced TNBC ("L1") in a patient having locally advanced TNBC by administering a combination therapy as described herein to the patient where the combination therapy is administered according to a dosing regimen comprising:
(i) administration of ipatasertib QD on day 1 through day 21;
(ii) administration of atezolizumab on day 1 and day 15;
(iii) administration of paclitaxel on day 1, day 8, and day 15; and
(iv) a rest period of at least 7 days.

In one embodiment of the first method (L1) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the first method (L1) of treating locally advanced TNBC the patient is administered at least 5 or at least 10 cycles of the dosing regimen.

In one embodiment provided herein is a second method of treating locally advanced TNBC ("L2") in a patient having locally advanced TNBC by administering a combination therapy as described herein to the patient where the combination therapy is administered according to a dosing regimen comprising:
(i) administration of ipatasertib QD on day 1 through day 21;
(ii) administration of atezolizumab on day 1 and day 15;
(iii) administration of nab-paclitaxel on day 1, day 8, and day 15; and
(iv) a rest period of at least 7 days.

In one embodiment of the second method (L2) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the second method (L2) of treating locally advanced TNBC the patient is administered at least 5 or at least 10 cycles of the dosing regimen.

In one embodiment provided herein is a third method of treating locally advanced TNBC ("L3") in a patient having locally advanced TNBC by administering a combination therapy as described herein to the patient where the combination therapy is administered according to a dosing regimen comprising:
(i) administration of ipatasertib QD on day 1 through day 21;
(ii) administration of atezolizumab on day 15;
(iii) administration of paclitaxel on day 1, day 8, and day 15; and
(iv) a rest period of at least 7 days.

In one embodiment of the third method (L3) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the third method (L3) of treating locally advanced TNBC the patient is administered at least 5 or at least 10 cycles of the dosing regimen.

In one embodiment provided herein is a fourth method of treating locally advanced TNBC ("L4") in a patient having locally advanced TNBC by administering a combination therapy as described herein to the patient where the combination therapy is administered according to a dosing regimen comprising:
(i) administration of ipatasertib QD on day 1 through day 21;
(ii) administration of atezolizumab on day 15;
(iii) administration of nab-paclitaxel on day 1, day 8, and day 15; and
(iv) a rest period of at least 7 days.

In one embodiment of the fourth method (L4) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the fourth method (L4) of treating locally advanced TNBC the patient is administered at least 5 or at least 10 cycles of the dosing regimen.

In another embodiment provided herein is a fifth method of treating locally advanced TNBC ("L5") in a patient having locally advanced TNBC by administering a combination therapy as described herein to the patient where the combination therapy is administered according to a dosing regimen comprising:
(i) administration of atezolizumab on day 1 and day 15;
(ii) administration of paclitaxel on day 1, day 8, and day 15;
(iii) administration of ipatasertib QD on day 15 through day 21; and
(iv) a rest period of at least 7 days.

In one embodiment of the fifth method (L5) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

In another embodiment of the fifth method (L5) of treating locally advanced TNBC the patient is administered at least 5 or at least 10 cycles of the dosing regimen.

In still another embodiment provided herein is a sixth method of treating locally advanced TNBC ("L6") in a patient having locally advanced TNBC by administering a combination therapy as described herein to the patient where the combination therapy is administered according to a dosing regimen comprising:
(i) administration of atezolizumab on day 1 and day 15;
(ii) administration of nab-paclitaxel on day 1, day 8, and day 15;
(iii) administration of ipatasertib QD on day 15 through day 21; and
(iv) a rest period of at least 7 days.

In one embodiment of the sixth method (L6) of treating locally advanced TNBC the dosing regimen further comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

In another embodiment of the sixth method (L6) of treating locally advanced TNBC the patient is administered at least 5 or at least 10 cycles of the dosing regimen.

In one embodiment, treatment with a combination therapy according to the methods provided herein increases a patient's OS by 3, 4, 5, 6, 7, 8, 9, 10, 15, 20 or more months comparable to non-treatment or SOC treatment. In one embodiment, treatment with a combination therapy according to the methods provided herein increases the patient's amount of ORR. In another embodiment, the TTP is increased in a patient following treatment with a combination therapy according to the methods provided herein. In another embodiment, the PFS is increased in a patient following treatment with a combination therapy according to the methods provided herein. In one embodiment provided herein a patient is diagnosed having a CR following treatment with a combination therapy according to the methods provided herein. In one embodiment provided herein a patient is diagnosed having a PR following treatment with a combination therapy according to the methods provided herein. In one embodiment provided herein a patient is diagnosed having SD following treatment with a combination therapy according to the methods provided herein.

In one embodiment of the methods described herein, a patient has been treated with one or more cancer therapies before administration of a combination therapy described herein. In one embodiment of the methods described herein, the prior therapy comprises atezolizumab and/or a taxane (e.g. paclitaxel or nab-paclitaxel). In one embodiment of the methods described herein, a patient has breast cancer described herein that is resistant to one or more cancer therapies. In one embodiment of the methods described herein, resistance to cancer therapy includes recurrence of cancer or refractory cancer. Recurrence may refer to the reappearance of cancer, in the original site or a new site, after treatment. In one embodiment of the methods described herein, resistance to a cancer therapy includes progression of the cancer during treatment with the anticancer therapy. In some embodiments of the methods described herein, resistance to a cancer therapy includes cancer that does not response to treatment. The cancer may be resistant at the beginning of treatment or it may become resistant during treatment. In some embodiments of the methods described herein, the cancer is at early stage or at late stage.

Systemic chemotherapy is the standard treatment for patients with metastatic TNBC, although no standard regimen or sequence exists. Single-agent cytotoxic chemotherapeutic agents as shown in Table 1 are generally regarded as the primary option for patients with metastatic TNBC, although combination chemotherapy regimens such as those shown in Table 2 may be used, for instance when there is aggressive disease and visceral involvement. In one embodiment of the methods described herein, a patient described herein (e.g. a patient having MTNBC or locally advanced TNBC as described herein) can be previously treated with one or more of the single agent therapies as set forth in Table 1 prior to administration of a combination therapy described herein. In one embodiment of the methods described herein, a patient described herein can have MTNBC or locally advanced TNBC as described herein that is resistant to one or more of the single agent therapies as set forth in Table 1.

TABLE 1

Single agent chemotherapy regimens

| Class | Agents |
|---|---|
| Anthracyclines | Doxorubicin |
|  | Pegylated liposomal doxorubicin |
|  | Epirubicin |
| Taxanes | Paclitaxel |
|  | Docetaxel |
|  | Albumin-bound paclitaxel (nab-paclitaxel) |
| Anti-metabolites | Capecitabine |
|  | Gemcitabine |
| Non-taxane microtubule inhibitors | Vinorelbine |
|  | Eribulin |
|  | Ixabepilone |
| Platinum | Carboplatin |
|  | Cisplatin |
| Alkylating agent | Cyclophosphamide |

Also provided herein are methods wherein a patient described herein (e.g. a patient having MTNBC or locally advanced TNBC as described herein) has been previously treated with a combination therapy such as those set forth in Table 2 prior to administration of a combination therapy described herein.

TABLE 2

Combination chemotherapy regimens

| Class | Agents | Shorthand |
|---|---|---|
| Anthracycline and alkylating agent followed by taxane | Doxorubicin + cyclophosphamide followed by a taxane (e.g., docetaxel or paclitaxel) | AC→ T |
| Anthracycline and alkylating agent | Doxorubicin + cyclophosphamide (or liposomal doxorubicin + cyclophosphamide) | AC |
|  | Epirubicin + cyclophosphamide | EC |
| Taxane, anthracycline, and alkylating agent | Docetaxel + doxorubicin + cyclophosphamide | TAC |
| Taxane and alkylating agent | Docetaxel + cyclophosphamide | TC |
| Alkylating agent, methotrexate and anti-metabolite | Cyclophosphamide + methotrexate + fluorouracil | CMF |
| Anti-metabolite, anthracycline, and alkylating agent | Fluorouracil + doxorubicin + cyclophosphamide | FAC |
|  | Fluorouracil + epirubicin + cyclophosphamide | FEC |
| Anti-metabolite, anthracycline, and alkylating agent followed by taxane | Fluorouracil + epirubicin + cyclophosphamide followed by docetaxel or paclitaxel | FEC/CEF→T |
|  | Fluorouracil + doxorubicin + cyclophosphamide followed by paclitaxel | FAC→T |

TABLE 2-continued

Combination chemotherapy regimens

| Class | Agents | Shorthand |
|---|---|---|
| Taxane and anti-metabolite | Docetaxel + capecitabine, or Paclitaxel + gemcitabine | GT |
| Anti-metabolite and platinum | Gemcitabine + carboplatin |  |
| Anti-metabolite and non-taxane microtubule inhibitor | Capecitibine + vinorelbine Gemcitabine + vinorelbine |  |
| Taxane and VEGF inhibitor (e.g., anti-VEGF antibody) | Paclitaxel + bevacizumab |  |

In one embodiment of the methods described herein, a patient having MTNBC or locally advanced TNBC as described herein may have undergone surgical treatment such as, for example, surgery that is breast-conserving (i.e., a lumpectomy, which focuses on removing the primary tumor with a margin), or more extensive (i.e., mastectomy, which aims for complete removal of all of the breast tissue) prior to administration of a combination therapy described herein. In another embodiment, a patient described herein may undergo surgical treatment following treatment with a combination therapy described herein. In one embodiment, where patients undergo surgical treatment after treatment with a combination therapy described herein, such patients have a greater success of complete response compared to treatment with a double combination (e.g. ipatasertib/paclitaxel or atezolizumab/paclitaxel) or monotherapy treatment.

Radiation therapy is typically administered post-surgery to the breast/chest wall and/or regional lymph nodes, with the goal of killing microscopic cancer cells left post-surgery. In the case of a breast conserving surgery, radiation is administered to the remaining breast tissue and sometimes to the regional lymph nodes (including axillary lymph nodes). In the case of a mastectomy, radiation may still be administered if factors that predict higher risk of local recurrence are present. In some embodiments of the methods provided herein a patient having MTNBC or locally advanced TNBC as described herein may have received radiation therapy prior to administration of a combination therapy described herein. In other embodiments of the methods provided herein a patient having MTNBC or locally advanced TNBC as described herein may have receive radiation therapy following administration of a combination therapy described herein.

In one preferred embodiment provided herein is a method of treating a patient described herein having MTNBC described herein by administering a combination therapy comprising ipatasertib at 400 mg, atezolizumab at 840 mg, and paclitaxel at 80 mg/m$^2$ according to M1 as described herein. In a preferred embodiment provided herein is a method of treating a patient described herein having MTNBC described herein by administering a combination therapy comprising ipatasertib at 400 mg, atezolizumab at 840 mg, and nab-paclitaxel at 100 mg/m$^2$ according to M2 as described herein.

In one preferred embodiment provided herein is a method of treating a patient described herein having locally advanced TNBC described herein by administering a combination therapy comprising ipatasertib at 400 mg, atezolizumab at 840 mg, and paclitaxel at 80 mg/m$^2$ according to L1 as described herein. In a preferred embodiment provided herein is a method of treating a patient described herein having locally advanced TNBC described herein by administering a combination therapy comprising ipatasertib at 400 mg, atezolizumab at 840 mg, and nab-paclitaxel at 100 mg/m$^2$ according to L2 as described herein.

Also provided herein are methods of inhibiting tumor growth or producing tumor regression in a patient described herein by administering a combination therapy described herein. In one embodiment provided herein is a method of inhibiting tumor growth in a patient having MTNBC described herein by administering a combination therapy comprising M1 or M2 as described herein. In one embodiment provided herein is a method of inhibiting tumor growth in a patient having MTNBC described herein by administering a combination therapy comprising M3 or M4 as described herein. In one embodiment provided herein is a method of inhibiting tumor growth in a patient having MTNBC described herein by administering a combination therapy comprising M5 or M6 as described herein.

In another embodiment provided herein is a method of inhibiting tumor growth in a patient having locally advanced TNBC described herein by administering a combination therapy comprising L1 or L2 as described herein. In another embodiment provided herein is a method of inhibiting tumor growth in a patient having locally advanced TNBC described herein by administering a combination therapy comprising L3 or L4 as described herein. In another embodiment provided herein is a method of inhibiting tumor growth in a patient having locally advanced TNBC described herein by administering a combination therapy comprising L5 or L6 as described herein.

In one embodiment provided herein is a method of producing or improving tumor regression in a patient having MTNBC described herein by administering a combination therapy comprising M1 or M2 as described herein. In one embodiment provided herein is a method of producing or improving tumor regression in a patient having MTNBC described herein by administering a combination therapy comprising M3 or M4 as described herein. In one embodiment provided herein is a method of producing or improving tumor regression in a patient having MTNBC described herein by administering a combination therapy comprising M5 or M6 as described herein.

In one embodiment provided herein is a method of producing or improving tumor regression in a patient having locally advanced TNBC described herein by administering a combination therapy comprising L1 or L2 as described herein. In one embodiment provided herein is a method of producing or improving tumor regression in a patient locally advanced TNBC described herein by administering a combination therapy comprising L3 or L4 as described herein. In one embodiment provided herein is a method of producing or improving tumor regression in a patient having locally advanced TNBC described herein by administering a combination therapy comprising L5 or L6 as described herein.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. ipatasertib, atezolizumab, and paclitaxel or nab-paclitaxel) is administered in a dosing regimen comprising a staggered dosing schedule.

In one embodiment of the methods described herein, the dosing regimen reduces the number or frequency of grade 2 or grade 3 or higher grade adverse event comparable to administration of an ipatasertib and paclitaxel or nab-paclitaxel combination or comparable to administration of an atezolizumab and paclitaxel or nab-paclitaxel combination.

In another embodiment of the methods described herein the dosing reduces the number or frequency of grade 2 or grade 3 or higher grade adverse event comparable to administration of either agent alone.

It is generally understood that the when an adverse event occurs, four options exist: (1) continue treatment as-is with optional concomitant therapy; (2) adjust the dose of one or more agents in the dosing regiment; (3) suspend administration of one or more agents in the dosing regimen; or (4) discontinue administration of one or more agents in the dosing regimen.

In one embodiment of the methods described herein, a patient described herein experiences one or more adverse events comprising nausea, vomiting, diarrhea, stomatitis/mucosal inflammation, asthenia/fatigue, hyperglycemia, peripheral neuropathy, rash, neutropenia, IRRs, immune-related hepatitis, pneumonitis, colitis, pancreatitis, diabetes mellitus, hypothyroidism, hyperthyroidism, adrenal insufficiency, Guillain-Barré syndrome, hypophysitis, myasthenic syndrome or myasthenia gravis, meningoencephalitis, myocarditis, nephritis, alopecia, anemia, thrombocytopenia, cranial nerve palsies, myalgia, arthralgia, myocardial disorders, cardiac failure, angina, tachycardia, ventricular arrhythmia, cystoid macular edema, Stevens-Johnson syndrome/toxic epidermal necrolysis, sepsis, drug-induced liver injury, acute renal failure, hemolytic-uremic syndrome, or drug-induced lupus erythematous. In one embodiment, the adverse event(s) experienced by a patient described herein undergoing treatment with a combination therapy described herein are comparably reduced as described herein.

In another embodiment of the methods described herein, the adverse event is selected from the group consisting of gastrointestinal, dermatologic, hepatic, pulmonary, and hyperglycemia events.

In another embodiment of the methods described herein, the adverse event is (i) Diarrhea; (ii) Asthenia (fatigue); (iii) Nausea; (iv) Peripheral neuropathy (e.g. peripheral sensory neuropathy, neuropathy peripheral, or peripheral motor neuropathy); (v) Neutropenia (e.g. decreased neutrophil count or febrile neutropenia); (vi) Rash (e.g. maculo-papular, erythema, urticarial, dermatitis, rash popular, skin exfoliation, or toxic skin eruption); (vii) Vomiting; (viii) Oral mucositis (e.g. stomatitis, mucosal inflammation, mouth inflammation, or mouth ulceration); (ix) Hyperlipidemia (e.g. hypercholesterolemia, hypertriglyceridemia, hyperlipidemia, increased blood cholesterol, or increased blood triglycerides); (x) Hepatotoxicity (e.g. ALT or increased AST); (xi) Hyperglycemia (e.g. increased blood glucose); (xii) Pneumonia (e.g. lower respiratory tract infection), or (xiii) Pneumonitis (e.g. interstitial lung diseases).

In still another embodiment of the methods described herein, the adverse event is diarrhea, nausea, neutropenia, decreased neutrophil count, peripheral neuropathy, or fatigue. In one embodiment of the methods described herein, a patient described herein experiences an adverse event comprising diarrhea. In one embodiment of the methods described herein, less than 75%, 60%, 50%, 40%, 33%, 25%, 20% 12% or 5% of all patients treated experience diarrhea from treatment with a combination therapy described herein. In one embodiment of the methods described herein, less than 85%, 75%, 60%, 50%, 40%, 33%, 25%, 20% 17%, 10% or 5% of all patients treated experience a rash as described herein from treatment with a combination therapy described herein. In one embodiment of the methods described herein, less than 60%, 50%, 45%, 33%, 25%, 10% or 5% of all patients treated experience nausea from treatment with a combination therapy described herein. In one embodiment of the methods described herein, less than 50%, 40%, 33%, 25%, 20% 17%, 10% or 8% of all patients treated experience neutropenia as described herein from treatment with a combination therapy described herein.

In one particular embodiment of the methods described herein the adverse event is diarrhea, rash, or neutropenia. In a preferred embodiment, the adverse event is rash (Grade 3 or higher), wherein the dosing regimen described herein (e.g. M1, M2, L1, or L2) is not altered (i.e. the amount of the agents and/or the timing of administration is not changed when a patient described herein experiences a Grade 3 adverse event comprising a rash). In one embodiment, a patient having such rash is administered antihistamines (therapeutically or prophylactically). In another embodiment, a patient having such rash is administered a steroid. In a further preferred embodiment, the adverse event is erythema multiform (Grade 3 or higher), wherein the dosing regimen described herein (e.g. M1, M2, L1, or L2) is not altered as provided herein.

In another particular embodiment, the adverse event is diarrhea or neutropenia (Grade 3 or higher) wherein the dosing regimen described herein (e.g. M1, M2, L1, or L2) is not altered (i.e. the amount of the agents and/or the timing of administration is not changed when a patient described herein experiences a Grade 3 adverse event comprising diarrhea or neutropenia).

In one preferred embodiment, the adverse event is immune-mediated nephritis. In one embodiment, when a patient experiences an adverse event comprising immune-mediated nephritis, the dosing regimen described herein (e.g. M1, M2, L1, or L2) is not altered (i.e. the amount of the agents and/or the timing of administration is not changed. In another embodiment, atezolizumab administration as described herein can be suspended for about 80-110 days when a patient experiences an adverse event comprising immune-mediated nephritis. In a particular embodiment, atezolizumab administration as described herein can be suspended for about 84 days when a patient experiences an adverse event comprising immune-mediated nephritis.

In one embodiment of the methods described herein, a patient described herein does not have Type I or Type II diabetes mellitus requiring insulin. In another embodiment of the methods described herein, a patient described herein does not have lung disease selected from the group consisting of pneumonitis, interstitial lung disease, idiopathic pulmonary fibrosis, cystic fibrosis, Aspergillosis, and active tuberculosis. In still another embodiment of the methods described herein, a patient described herein does not have an autoimmune disease or an immune deficiency selected from the group consisting of myasthenia gravis, myositis, autoimmune hepatitis, systemic lupus erythematosus, rheumatoid arthritis, inflammatory bowel disease, antiphospholipid antibody syndrome, Wegener granulomatosis, Sjögren's syndrome, Guillain-Barré syndrome, and multiple sclerosis.

In one embodiment of the methods described herein, a patient described herein has not received allogeneic stem cell treatment prior to administration of a combination therapy described herein. In one embodiment of the methods described herein, a patient described herein has not received a prior solid organ transplantation prior to administration of a combination therapy described herein. In still another embodiment of the methods described herein, a patient described herein has not taken a systemic immunosuppressive medication selected from the group consisting of corticosteroids, cyclophosphamide, azathioprine, methotrexate, thalidomide, and anti-tumor necrosis factor alpha agents within 2 weeks prior to administration of a combination therapy described herein.

Concomitant Therapies

Concomitant therapy as used herein includes any medication (e.g., prescription drugs, over-the-counter drugs, vaccines, herbal or homeopathic remedies, nutritional supplements) used by a patient in addition to the agents described herein (e.g. ipatasertib, atezolizumab, and paclitaxel or nab-paclitaxel) from about 14 days prior to administration of the first agent of the first cycle as set forth herein.

In one embodiment of the methods described herein, a patient can concomitantly take one or more of the following medications: (i) oral contraceptives; (ii) palliative radiotherapy (e.g., treatment of known bony metastases or symptomatic relief of pain) provided it does not interfere with the assessment of tumor target lesions (e.g., the lesion to be irradiated must not be the only site of measurable disease); (iii) anti-convulsant therapy; (iv) antihistamines; (v) anti-pyretics; (vi) analgesics (e.g. acetaminophen, ibuprofen); (vii) loperamide; (viii) granulocyte colony-stimulating factor; (ix) bisphosphonate or denosumab maintenance therapy; (x) luteinizing hormone-releasing hormone agonists (e.g. for ovarian function preservation); (xi) prophylactic or therapeutic anticoagulation therapy; (xii) inactivated influenza vaccinations; (xiii) megestrol acetate; (xiv) mineralocorticoids; (xv) inhaled corticosteroids (e.g. for COPD or asthma); (xvi) low-dose corticosteroids (e.g. for orthostatic hypotension or adrenocortical insufficiency); (xvii) low-dose systemic immunosuppressants; (xviii) diphenhydramine; (xix) H2-receptor antagonists (e.g., famotidine); (xx) calcium-channel blockers; or (xxi) β-blockers; or a combination thereof.

In some embodiments of the methods described herein, administration of ipatasertib can be held for at least 7 days before and/or after palliative radiotherapy. In one embodiment of the methods described herein, administration of ipatasertib is held for at least 14 days after palliative radiotherapy.

In one embodiment of the methods described herein, patients administered a combination therapy described herein cannot concomitantly be administered: (i) another chemotherapy; (ii) hormonal therapy; (iii) another immunotherapy; (iv) radiotherapy (with the exception of palliative radiotherapy as provided herein); (v) quinidine or other anti-arrhythmic agents with narrow therapeutic index; (vi) live, attenuated vaccines (e.g., FLUMIST) within 4 weeks prior to initiation of study treatment, during treatment with atezolizumab, and for 5 months after the last dose of atezolizumab; or (vii) systemic immunostimulatory agents (including, but not limited to, interferons and interleukin 2) within 4 weeks or 5 half-lives of the drug, whichever is longer, prior to initiation of study treatment and during study treatment.

In one embodiment of the methods described herein, a patient can be male or female 18 years old or older at the time of treatment. In one embodiment, the patient is not younger than 18, 16, 14, 12, 10, or 5 years old. In one embodiment, the patient is older than 5, 10, 12, 14, 16, or 18 years old.

In one embodiment of the methods described herein, a patient has, at the time of starting administration of a combination therapy described herein, a measured adequate hematologic and organ function as defined by one or more of the following measurements:

a) Neutrophils (absolute neutrophil count [ANC] ≥1500/μL);
b) Hemoglobin ≥9 g/DI;
c) Platelet count ≥100,000/μL;
d) Serum albumin ≥3 g/DI;
e) Total bilirubin ≤1.5× the upper limit of normal (ULN) (except in patients with known Gilbert syndrome can have serum bilirubin ≤3×ULN);
f) AST and ALT ≤2.5×ULN (except in patients with documented liver or bone metastases can have AST and ALT ≤5×ULN);
g) ALP ≤2×ULN (except in (i) patients with known liver involvement can have ALP ≤5×ULN and (ii) patients with known bone involvement can have ALP ≤7×ULN);
h) PTT (or aPTT) and INR ≤1.5×ULN (except for patients receiving anticoagulation therapy);
i) Patients receiving heparin treatment should have a PTT (or aPTT) between 1.5 and 2.5×ULN (or patient value before starting heparin treatment);
j) Patients receiving coumarin derivatives should have an INR between 2.0 and 3.0 assessed in two consecutive measurements 1 to 4 days apart;
k) Serum creatinine <1.5×ULN or creatinine clearance ≥50 mL/min based on Cockcroft-Gault glomerular filtration rate estimation: or $$\frac{(140 - age) \times (weight\ in\ kg) \times 0.85\ (if\ female)}{72 \times (serum\ creatine\ in\ mg/dL)}$$

l) Fasting total serum glucose ≤150 mg/dL and glycosylated hemoglobin (HbA$_{1C}$) ≤7.5%.

Such measurements can be taken (e.g. within 7-14 days) before the first dose of any agent (e.g. Day 1 of Cycle 1 as set forth herein).

In one embodiment of the methods described herein, a patient has, at the time of starting administration life expectancy of at least 6 months.

Female patients treated using the combination therapies described herein should remain abstinent (refrain from heterosexual intercourse) or use contraceptive methods with a failure rate of <1% per year during the treatment period and for at least 28 days after the last dose of ipatasertib, 6 months after the last dose of paclitaxel, and 5 months after the last dose of atezolizumab, whichever occurs later. Male patients treated using the combination therapies described herein should remain abstinent (refrain from heterosexual intercourse) or use contraceptive measures.

In one embodiment of the methods described herein, TNBC (e.g. MTNBC or locally advanced TNBC) as described herein is histologically documented TNBC. In one embodiment of the methods described herein, a patient's receptor status at the start of administration corresponds to an evaluation of the most recent biopsy (non-fine-needle aspiration [FNA] sample) as assessed locally (or centrally, if not available locally) according to, for example, the ASCO/CAP guidelines. In another embodiment of the methods described herein, TNBC (e.g. MTNBC or locally advanced TNBC) as described herein is not amenable to resection with curative intent.

In one embodiment of the methods described herein, patients having treated brain or spinal cord metastases are administered a combination therapy described herein provided such patients have stable disease and are not on steroid treatment.

In one embodiment of the methods described herein, a combination therapy is not administered to a patient when such a patient has one or more of the following:
1) A history of malabsorption syndrome or other condition that interferes with enteral absorption or results in the inability or unwillingness to swallow pills;
2) An active infection requiring antibiotics;
3) A history of or current evidence of HIV infection;
4) Clinically significant history of liver disease consistent with Child-Pugh Class B or C (including, for example, active viral or other hepatitis (e.g., positive for hepatitis B surface antigen [HBsAg] or hepatitis C virus [HCV] antibody at screening), current drug or alcohol abuse, or cirrhosis);
5) Past hepatitis B virus (HBV) infection or resolved HBV infection
6) A positive result for HCV antibody (unless PCR is negative for HCV RNA);
7) A major surgical procedure, open biopsy, or significant traumatic injury within 28 days prior to Day 1 of Cycle 1 or anticipation of need for a major surgical procedure during the course of the study;
8) Is pregnant or breastfeeding, or intending to become pregnant during the study or within 28 days after the last dose of ipatasertib, 6 months after the last dose of paclitaxel, and 5 months after the last dose of atezolizumab, whichever occurs later;
9) A positive serum pregnancy test result within 3 days prior to initiation of study treatment;
10) New York Heart Association Class II, III, or IV heart failure, left ventricular ejection fraction <50%, or active ventricular arrhythmia requiring medication;
11) Current unstable angina or history of myocardial infarction within 6 months prior to Day 1 of Cycle 1;
12) Congenital long QT syndrome or screening QT interval corrected using Fridericia's formula (QTcF) >480 milliseconds;
13) A history or presence of an abnormal ECG that is clinically significant (e.g., complete left bundle branch block, second- or third-degree heart block, or evidence of prior myocardial infarction);
14) Treatment with approved or investigational cancer therapy within 14 days prior to Day 1 of Cycle 1; or
15) Prior treatment with an Akt inhibitor.

In another embodiment of the methods described herein, a combination therapy is not administered to a patient when such a patient has one or more of the following:
1) Confirmed leptomeningeal carcinomatosis;
2) Prior neoadjuvant or adjuvant chemotherapy and/or radiation treatment for early stage breast cancer (unless chemotherapy was completed ≥12 months prior to Day 1 of Cycle 1);
3) Treatment with previous systemic therapy for inoperable locally advanced or metastatic TNBC, including chemotherapy, immune checkpoint inhibitors, or targeted agents;
4) Unresolved, clinically significant toxicity from prior therapy, except for alopecia and Grade 1 peripheral neuropathy;
5) Uncontrolled pleural effusion, pericardial effusion, or ascites;
6) Uncontrolled tumor-related pain;
7) Symptomatic lesions (e.g., bone metastases or metastases causing nerve impingement) amenable to palliative radiotherapy should be treated prior to enrollment. Patients should be recovered from the effects of radiation (Grade 1 or better) prior to study enrollment. There is no required minimum recovery period beyond the 14 days required for radiation therapy;

8) Asymptomatic metastatic lesions whose further growth would likely cause functional deficits or intractable pain (e.g., bone metastasis) should be considered for loco-regional therapy;

9) Uncontrolled hypercalcemia (>1.5 mmol/L ionized calcium, >12 mg/dL calcium, or corrected serum calcium >ULN) or symptomatic hypercalcemia requiring continued use of bisphosphonate therapy;

10) A malignancy other than breast cancer within 5 years prior to Day 1 of Cycle 1 (except for appropriately treated carcinoma in situ of the cervix, non-melanoma skin carcinoma, or Stage I uterine cancer);

11) A history of Type I or Type II diabetes mellitus requiring insulin (unless administered a stable dose of oral diabetes medication(s) ≥2 weeks prior to Day 1 of Cycle 1);

12) Grade ≥2 uncontrolled or untreated hypercholesterolemia or hypertriglyceridemia;

13) A history of or active inflammatory bowel disease (e.g., Crohn's disease and ulcerative colitis) or active bowel inflammation (e.g., diverticulitis);

14) Lung disease (e.g. pneumonitis, interstitial lung disease, idiopathic pulmonary fibrosis, cystic fibrosis, aspergillosis, active tuberculosis, or history of opportunistic infections such as pneumocystis pneumonia or cytomegalovirus pneumonia);

15) Treatment with strong CYP3A inhibitors or strong CYP3A inducers within 2 weeks or 5 drug-elimination half-lives, whichever is longer, prior to initiation of study treatment;

16) Active or history of autoimmune disease or immune deficiency, including, but not limited to, myasthenia gravis, myositis, autoimmune hepatitis, systemic lupus erythematosus, rheumatoid arthritis, inflammatory bowel disease, antiphospholipid antibody syndrome, psoriatic arthritis, Wegener granulomatosis, Sjögren's syndrome, Guillain-Barré syndrome, or multiple sclerosis (except for patients with a history of autoimmune-related hypothyroidism who are on thyroid-replacement hormone are eligible for the study; patients with eczema, psoriasis, lichen simplex chronicus, or vitiligo with dermatologic manifestations only are eligible for the study provided (i) rash must cover <10% of body surface area, (ii) the disease is well controlled at baseline and requires only low-potency topical corticosteroids, and (iii) there is no occurrence of acute exacerbations of the underlying condition requiring psoralen plus ultraviolet A radiation, methotrexate, retinoids, biologic agents, oral calcineurin inhibitors, or high-potency or oral corticosteroids within the previous 12 months);

17) A history of idiopathic pulmonary fibrosis, organizing pneumonia (e.g., bronchiolitis obliterans), drug-induced pneumonitis, idiopathic pneumonitis, or evidence of active pneumonitis on screening chest CT scan;

18) Prior allogeneic stem cell or solid organ transplantation;

19) Treatment with a live, attenuated vaccine within 4 weeks prior to initiation of study treatment, or anticipation of need for such a vaccine during treatment with atezolizumab or within 5 months after the last dose of atezolizumab;

20) A history of severe allergic anaphylactic reactions to chimeric or humanized antibodies or fusion proteins;

21) A known hypersensitivity to Chinese hamster ovary cell products or recombinant human antibodies;

22) Treatment with systemic immunostimulatory agents (including, but not limited to, interferon and interleukin 2) within 4 weeks or 5 half-lives of the drug (whichever is longer) prior to Day 1 Cycle 1; 23) Treatment with systemic immunosuppressive medication (including, but not limited to, corticosteroids, cyclophosphamide, azathioprine, methotrexate, thalidomide, and anti-tumor necrosis factor alpha agents) within 2 weeks prior to initiation of study treatment, or anticipation of need for systemic immunosuppressive medication during the course of the study (except for (i) patients who received acute, low-dose systemic immunosuppressant medication or a one-time pulse dose of systemic immunosuppressant medication (e.g., 48 hours of corticosteroids for a contrast allergy) and (ii) patients who received mineralocorticoids (e.g., fludrocortisone), corticosteroids for chronic obstructive pulmonary disease or asthma, or low-dose corticosteroids for orthostatic hypotension or adrenal insufficiency);

24) Known hypersensitivity or contraindication to any component of a combination therapy described herein, including the paclitaxel excipient macrogolglycerol ricinoleate; or 25) Grade ≥2 peripheral neuropathy.

Biomarkers

Breast cancer is a heterogeneous disease with many distinct subtypes as defined by molecular signatures and a diverse array of mutational profiles. In one embodiment, a patient can be tested for PIK3CA/AKT1/PTEN-alteration status. In one embodiment, a patient described herein can be tested for one or more of a phosphatase and tensin homolog (PTEN) mutation, loss of PTEN expression, a phosphatidylinositol-4,5-bisphosphate 3-kinase catalytic subunit alpha (PIK3CA) mutation, a protein kinase B alpha (AKT1) mutation, or a combination thereof. In another embodiment, samples of patients described herein can be assessed for additional biomarkers in an effort to identify factors that may correlate with the safety and efficacy of the study treatments.

In one embodiment of the methods described herein, NGS, whole genome sequencing (WGS), other methods, or a combination thereof can be used for DNA obtained from blood samples and tumor tissue from patients described herein. Such samples may be analyzed to identify germline (e.g., BRCA1/2) and somatic alterations that are predictive of response to study drug, are associated with progression to a more severe disease state, are associated with acquired resistance to study drug, or can increase the knowledge and understanding of disease biology. In another embodiment of the methods described herein, patients described herein can have cancer characterized by activation of PI3K/Akt signaling such as activating mutations in PIK3CA or AKT1 as well as through alterations in PTEN, such as those provided herein. In another embodiment, PIK3CA/AKT1/PTEN-altered tumor status will be determined using an NGS assay (e.g., Foundation Medicine, Inc. [FMI]). Review of PIK3CA/AKT1/PTEN-altered status in archival tissue and response measures can be performed on an ongoing basis. Expression of PD-L1 as provided herein can be measured using techniques known in the art such as, for example, immunohistochemistry (IHC).

Circulating tumor DNA (ctDNA) can be detected in the blood of cancer patients with epithelial cancers and may have diagnostic and therapeutic significance (Schwarzenbach et al. 2011). For example, the mutational status of tumor cells may be obtained through the isolation of ctDNA (Maheswaran S, et al. N Engl J Med 2008; 359:366-77), and ctDNA has been used to monitor treatment effectiveness in melanoma (Shinozaki M, et al. Clin Cancer Res 2007;

13:2068-74). Blood samples from patients described herein can be collected at screening, at time of first tumor assessment, and/or at the study completion/early termination visit. In one embodiment, the samples are used to evaluate oncogenic genetic alterations at baseline and to assess for the possible emergence of new alteration after treatment with ipatasertib, atezolizumab, and paclitaxel or nab-paclitaxel.

EMBODIMENTS

Provided below are exemplary embodiments of the invention.

Embodiment 1

A method of treating metastatic triple negative breast cancer (MTNBC) in a patient having MTNBC, the method comprising administering to the patient a combination therapy comprising:
(i) ipatasertib;
(ii) atezolizumab; and
(iii) paclitaxel or nab-paclitaxel,
wherein said combination therapy is administered over a 28-day cycle.

Embodiment 2

A method of treating locally advanced triple negative breast cancer (TNBC) in a patient having locally advanced TNBC, the method comprising administering to the patient a combination therapy comprising:
(i) ipatasertib;
(ii) atezolizumab; and
(iii) paclitaxel or nab-paclitaxel,
wherein said combination therapy is administered over a 28-day cycle.

Embodiment 3

The method of embodiment 1 or 2, wherein ipatasertib is administered at an amount of 400 mg.

Embodiment 4

The method of embodiment 3, wherein the amount of ipatasertib administered to the patient is reduced to 300 mg or 200 mg.

Embodiment 5

The method of any one of embodiments 1-4, wherein atezolizumab is administered at an amount of 840 mg by intravenous (IV) infusion.

Embodiment 6

The method of any one of embodiments 1-5, wherein the combination therapy comprising administration of paclitaxel administered at an amount of 80 mg/m$^2$ by intravenous (IV) infusion.

Embodiment 7

The method of embodiment 6, wherein the amount of paclitaxel administered is reduced to 65 mg/m$^2$.

Embodiment 8

The method of any one of embodiments 1-5, wherein the combination therapy comprises administration of nab-paclitaxel administered at an amount of 100 mg/m$^2$ by intravenous (IV) infusion.

Embodiment 9

The method of embodiment 8, wherein the amount of nab-paclitaxel administered is reduced to 75 mg/m$^2$ or 50 mg/m$^2$.

Embodiment 10

The method of any one of embodiments 1-9, wherein the combination therapy is administered according to a dosing regimen comprising one 28-day cycle.

Embodiment 11

The method of any one of embodiments 1-10, wherein the dosing regimen comprises a first administration period followed by 2-24 cycles of 28-day administration periods.

Embodiment 12

The method of embodiment 10 or embodiment 11, wherein cycle 1 of dosing regimen comprises:
(i) administration of ipatasertib QD on day 1 through day 21;
(ii) administration of atezolizumab on day 1 and day 15;
(iii) administration of paclitaxel on day 1, day 8, and day 15; and
(iv) a rest period of at least 7 days.

Embodiment 13

The method of embodiment 12, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

Embodiment 14

The method of embodiment 10 or embodiment 11, wherein cycle 1 of dosing regimen comprises:
(i) administration of ipatasertib QD on day 1 through day 21;
(ii) administration of atezolizumab on day 1 and day 15;
(iii) administration of nab-paclitaxel on day 1, day 8, and day 15; and
(iv) a rest period of at least 7 days.

Embodiment 15

The method of embodiment 14, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;

(iii) administration of nab-paclitaxel on day 1, day 8, and day 15 of each of at least one more cycle; and
(iv) a rest period of at least 7 days.

Embodiment 16

The method of embodiment 10 or embodiment 11, wherein cycle 1 of dosing regimen comprises:
(i) administration of ipatasertib QD on day 1 through day 21;
(ii) administration of atezolizumab day 15;
(iii) administration of paclitaxel on day 1, day 8, and day 15; and
(iv) a rest period of at least 7 days.

Embodiment 17

The method of embodiment 16, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

Embodiment 18

The method of embodiment 10 or embodiment 11, wherein cycle 1 of dosing regimen comprises:
(i) administration of ipatasertib QD on day 1 through day 21;
(ii) administration of atezolizumab day 15;
(iii) administration of nab-paclitaxel on day 1, day 8, and day 15; and
(iv) a rest period of at least 7 days.

Embodiment 19

The method of embodiment 18, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

Embodiment 20

The method of embodiment 10 or embodiment 11, wherein cycle 1 of dosing regimen comprises:
(i) administration of atezolizumab on day 1 and day 15;
(ii) administration of paclitaxel on day 1, day 8, and day 15;
(iii) administration of ipatasertib QD on day 15 through day 21; and
(iv) a rest period of at least 7 days.

Embodiment 21

The method of embodiment 20, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of paclitaxel on day 1, day 8, and day 15 of each of at least one more cycle; and
(iv) a rest period of at least 7 days.

Embodiment 22

The method of embodiment 10 or embodiment 11, wherein cycle 1 of dosing regimen comprises:
(i) administration of atezolizumab on day 1 and day 15;
(ii) administration of nab-paclitaxel on day 1, day 8, and day 15;
(iii) administration of ipatasertib QD on day 15 through day 21; and
(iv) a rest period of at least 7 days.

Embodiment 23

The method of embodiment 22, wherein the dosing regimen comprises at least one more cycle comprising:
(i) administration of ipatasertib QD on day 1 through day 21 of each of at least one more cycle;
(ii) administration of atezolizumab on day 1 and day 15 of each of at least one more cycle;
(iii) administration of nab-paclitaxel on day 1, day 8, and day 15 of each of at least one more cycle; and
(iv) a rest period of at least 7 days.

Embodiment 24

A method of inhibiting tumor growth or producing/increasing tumor regression in a patient having MTNBC or locally advanced TNBC, the method comprising administering to the patient by administering a combination therapy according to the methods of any one of embodiments 1-23.

Embodiment 25

The method of any one of embodiments 1-24, wherein said patient experiences one or more adverse event selected from the group consisting of nausea, vomiting, diarrhea, stomatitis/mucosal inflammation, asthenia/fatigue, hyperglycemia, peripheral neuropathy, rash, neutropenia, IRRs, immune-related hepatitis, pneumonitis, colitis, pancreatitis, diabetes mellitus, hypothyroidism, hyperthyroidism, adrenal insufficiency, Guillain-Barré syndrome, hypophysitis, myasthenic syndrome or myasthenia gravis, meningoencephalitis, myocarditis, nephritis, l alopecia, anemia, thrombocytopenia, cranial nerve palsies, myalgia, arthralgia, myocardial disorders, cardiac failure, angina, tachycardia, ventricular arrhythmia, cystoid macular edema, Stevens-Johnson syndrome/toxic epidermal necrolysis, sepsis, drug-induced liver injury, acute renal failure, hemolytic-uremic syndrome, erythema multiform, immune-mediated nephritis, and drug-induced lupus erythematous.

Embodiment 26

The method of embodiment 25, wherein the adverse event is rash.

Embodiment 27

The method of embodiment 25, wherein the adverse event is erythema multiform.

Embodiment 28

The method of embodiment 26 or embodiment 27, wherein the patient is administered antihistamines or steroids.

Embodiment 29

The method of embodiment 25, wherein the adverse event is diarrhea.

Embodiment 30

The method of embodiment 25, wherein the adverse event is neutropenia.

Embodiment 31

The method of embodiment 25, wherein the adverse event is immune-mediated nephritis.

Embodiment 32

The method of any one of embodiments 25-31, wherein the adverse event is grade 3 or higher.

Embodiment 33

The method of any one of embodiments 25-32, wherein dosing regimen is not altered.

Embodiment 34

The method of embodiment 33, wherein the same amount of each agent and/or the timing of administration of the agents is not altered.

Embodiment 35

The method of any one of embodiments 1-34, wherein said patient has TNBC determined to have a phosphatase and tensin homolog (PTEN) mutation, loss of PTEN expression, a phosphatidylinositol-4,5-bisphosphate 3-kinase catalytic subunit alpha (PIK3CA) mutation, a protein kinase B alpha (AKT1) mutation, or a combination thereof.

Embodiment 36

The method of embodiment 35, wherein the loss of PTEN expression is hemizygous or homozygous.

Embodiment 37

The method of any one of embodiments 1-36, wherein the patient does not have Type I or Type II diabetes mellitus requiring insulin.

Embodiment 38

The method of any one of embodiments 1-37, wherein the patient does not have lung disease selected from the group consisting of pneumonitis, interstitial lung disease, idiopathic pulmonary fibrosis, cystic fibrosis, Aspergillosis, and active tuberculosis.

Embodiment 39

The method of any one of embodiments 1-38, wherein the patient does not have an autoimmune disease or an immune deficiency selected from the group consisting of myasthenia gravis, myositis, autoimmune hepatitis, systemic lupus erythematosus, rheumatoid arthritis, inflammatory bowel disease, antiphospholipid antibody syndrome, Wegener granulomatosis, Sjögren's syndrome, Guillain-Barré syndrome, and multiple sclerosis.

Embodiment 40

The method of any one of embodiments 1-39, wherein the patient has not received allogeneic stem cell treatment.

Embodiment 41

The method of any one of embodiments 1-40, wherein the patient has not received a prior solid organ transplantation.

Embodiment 42

The method of any one of embodiments 1-41, wherein the patient has not taken a systemic immunosuppressive medication selected from the group consisting of corticosteroids, cyclophosphamide, azathioprine, methotrexate, thalidomide, and anti-tumor necrosis factor alpha agents within 2 weeks prior to administration of the combination therapy.

The following Examples are presented by way of illustration, not limitation.

EXAMPLES

Patients were screened prior to administration of a combination therapy described herein and again at each subsequent tumor evaluation. Response was assessed by the investigator on the basis of physical examinations (with photography measurements) and imaging (CT, MRI, and bone scans) through use of RECIST v1.1 and immune-modified RECIST.

Tumor assessments were performed based on a schedule calculated from Cycle 1, Day 1 (study Day 1) with the first assessment during Week 8 and every 8 weeks thereafter, regardless of treatment administration timings or prior early/late tumor assessments. Therefore, the window for each scan was the 7 days of the given week. For patients with known or suspected bone metastasis, follow-up bone scans were performed during Days 16-28 of every fourth cycle (every 16 weeks). Bone disease and any changes in bone imaging were evaluated radiographically by CT scan, MRI, or X-ray to ascertain the presence of bone destruction versus a healing reaction.

Systemic immune activation is a rare condition characterized by an excessive immune response. Given the mechanism of action of atezolizumab, systemic immune activation is considered a potential risk when given in combination with other immunomodulating agents. Systemic immune activation was included in the differential diagnosis for patients who, in the absence of an alternative etiology, developed a sepsis-like syndrome after administration of atezolizumab.

A total of eighteen (18) patients (Table 3) were treated according to treatment regimen 1 as provided in FIG. 1 that included treatment with ipatasertib, paclitaxel, and atezolizumab ("Arm A"). For clarity, Arm A includes administration of 400 mg ipatasertib PO QD on days 1-21, administration of 840 mg atezolizumab IV on days 1 and 15, and administration of 80 mg/m$^2$ paclitaxel IV on days 1, 8, and 15—followed by a 7-day rest period. The 28-day cycle is repeated until loss of clinical benefit, unacceptable toxicity, consent withdrawal, or in certain instances complete remission. Tumour assessments were performed at baseline, and every 8 weeks thereafter. Among the patients, no patient discontinued treatment before the first tumour assessment. "Efficacy evaluable" as used herein refers to patients that have undergone an eight (8) week tumor assessment. "Confirmed efficacy evaluable" refers to patients that have undergone a sixteen (16) week tumor assessment.

A total of eight (8) patients (Table 3) were treated according to treatment regimen 1 as provided in FIG. 1 that included treatment with ipatasertib, nab-paclitaxel, and atezolizumab ("Arm B"). For clarity, Arm B includes administration of 400 mg ipatasertib PO QD on days 1-21, administration of 840 mg atezolizumab IV on days 1 and 15, and administration of 100 mg/m2 nab-paclitaxel IV on days 1, 8, and 15—followed by a 7-day rest period. The 28-day cycle is repeated until loss of clinical benefit, unacceptable toxicity, consent withdrawal, or in certain instances complete remission. Tumour assessments were performed at baseline, and every 8 weeks thereafter.

TABLE 3

Response rates for treatment

| | No. of Patients (n) | No. of Patients Efficacy Evaluable (n) | BORR (CR/PR) [SD/PD] |
|---|---|---|---|
| Patient Set 1 (Arm A) (Ipat/atezo/pac) | 18 | 18 | 12/18 (0/12) [4/2] |
| Patient Set 2 (Arm B) (Ipat/atezo/nab-pac) | 8 | 8 | 7/8 (0/7) [1/0] |
| Total Set 1, Set 2 | 26 | 26 | 19/26 (0/19) [5/2] |

Abbreviations; ipat = ipatasertib; atezo = atezolizumab; pac = paclitaxel; nab-pac = nab-paclitaxel; CR = complete response; PR = partial response; SD = stable disease; PD = progressive disease; BORR = best overall response rate Among the total twenty six (26) efficacy evaluable patients there were a total of nineteen (19) confirmed responses, giving an ORR of 73% (95% CI 53-88%), see FIG. 6. The responses appear to be durable and irrespective of tumor alterations status as discussed below, See FIG. 6 and FIG. 7.

Comparatively, the treated patients of the ipatasertib/atezolizumab/taxane combination therapies described herein resulted in greater benefit than monotherapy, combination of ipatasertib with a taxane, and combination of atezolizumab with a taxane. For example, in the ITT populations of a phase 2 clinical study including ipatasertib and paclitaxel, a (confirmed) ORR=40% was reported. (LOTUS Trial.) Similarly, patient populations in a phase 3 clinical study including atezolizumab and nab-paclitaxel reported an unconfirmed response rate of 56%. (Impassion130.) Confirmed response rate was not reported in the latter study (Schmid P1, Adams S1, Rugo H S1, et al., 2018 and Kim S.-B., Dent R., Im S.-A., et al., 2017). When compared to the values of Table 3 above, the combination therapy herein is superior to previous combination therapies.

Figure 4A:
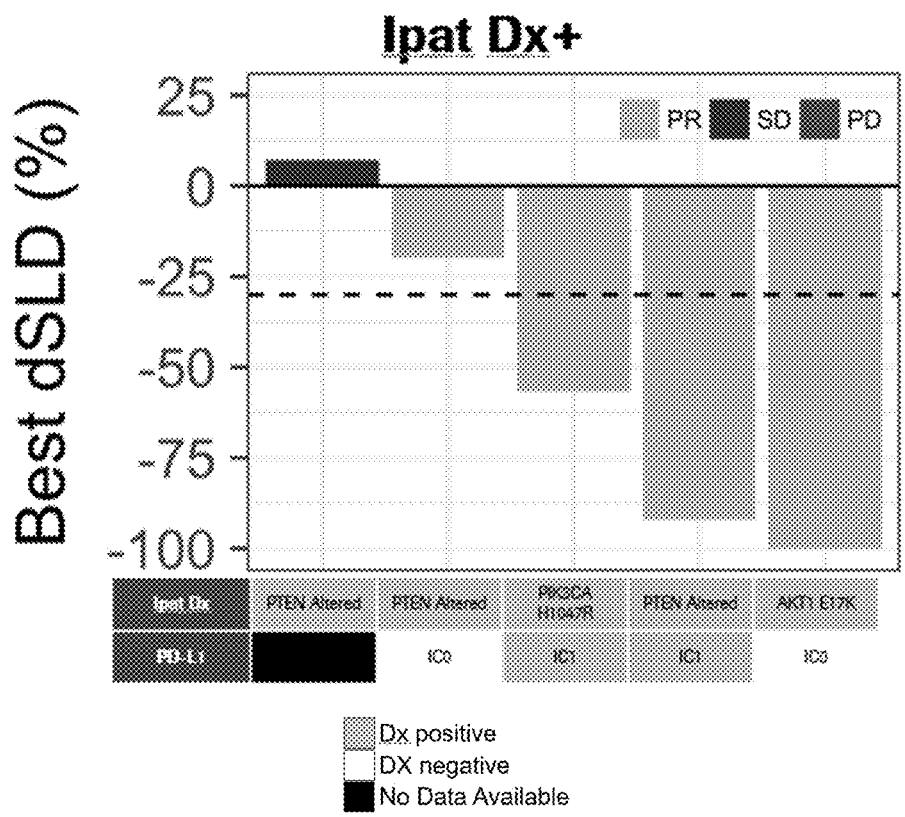
FIG. 4A and FIG. 4B depict the patient response annotated to indicate the diagnostic status for both PIK3CA/AKT1/PTEN-alterations (e.g. diagnostic positive (FIG. 4A) or diagnostic negative (FIG. 4B)), as determined by next-generation sequencing (NGS), as well as PD-L1 expression, as measured by immunohistochemistry. dSLD=change in sum of longest distances; PR=partial response; SD=stable disease; PD=progressive disease; ipat=ipatasertib; Neg=negative.
Figure 4B:
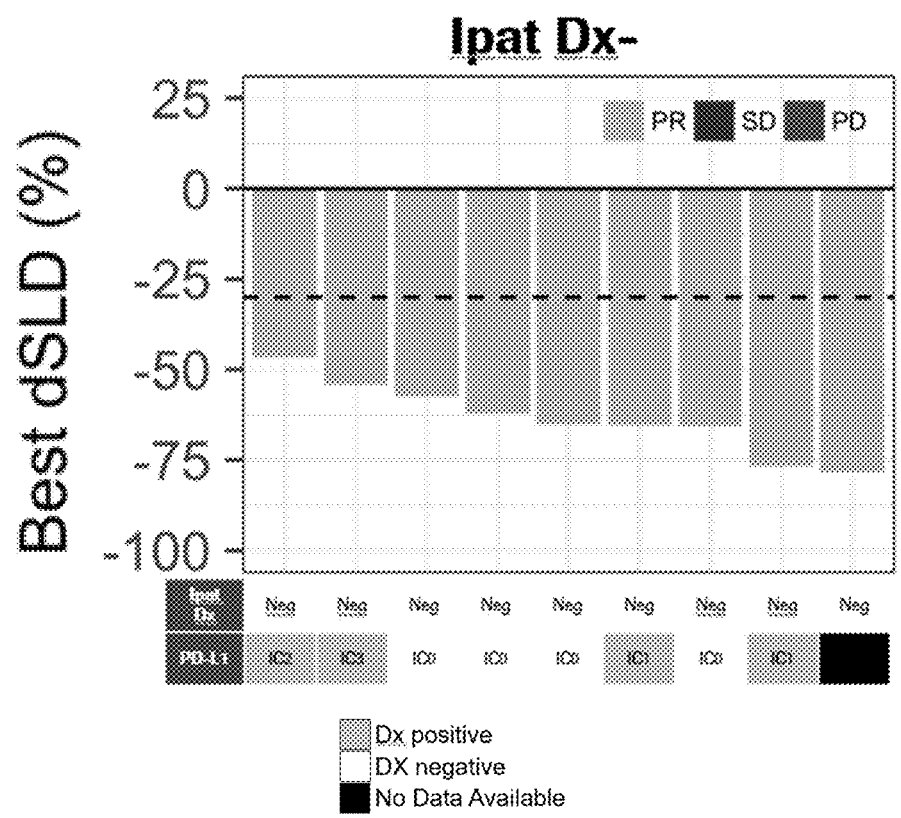
Figure 5A:
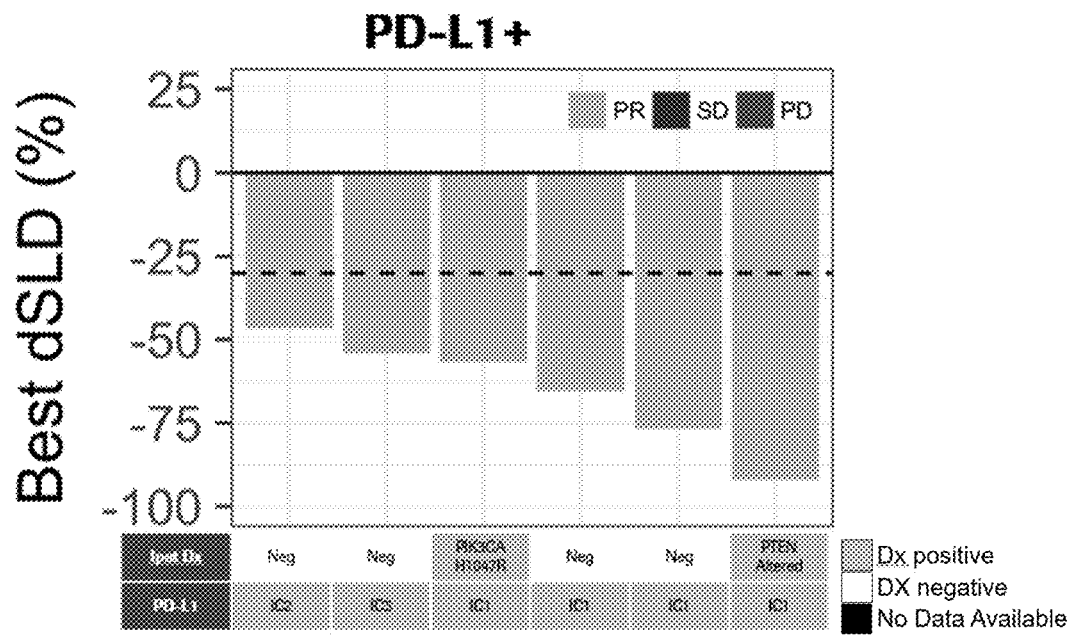
FIG. 5A depicts patient response annotated to indicate the diagnostic status for both PD-L1 expression (e.g. diagnostic positive (FIG. 5A) or diagnostic negative (FIG. 5B)), as measured by immunohistochemistry and PIK3CA/AKT1/PTEN-alterations as determined by next-generation sequencing (NGS). dSLD=change in sum of longest distances; PR=partial response; SD=stable disease; PD=progressive disease; ipat=ipatasertib; Neg=negative.
Figure 5B:
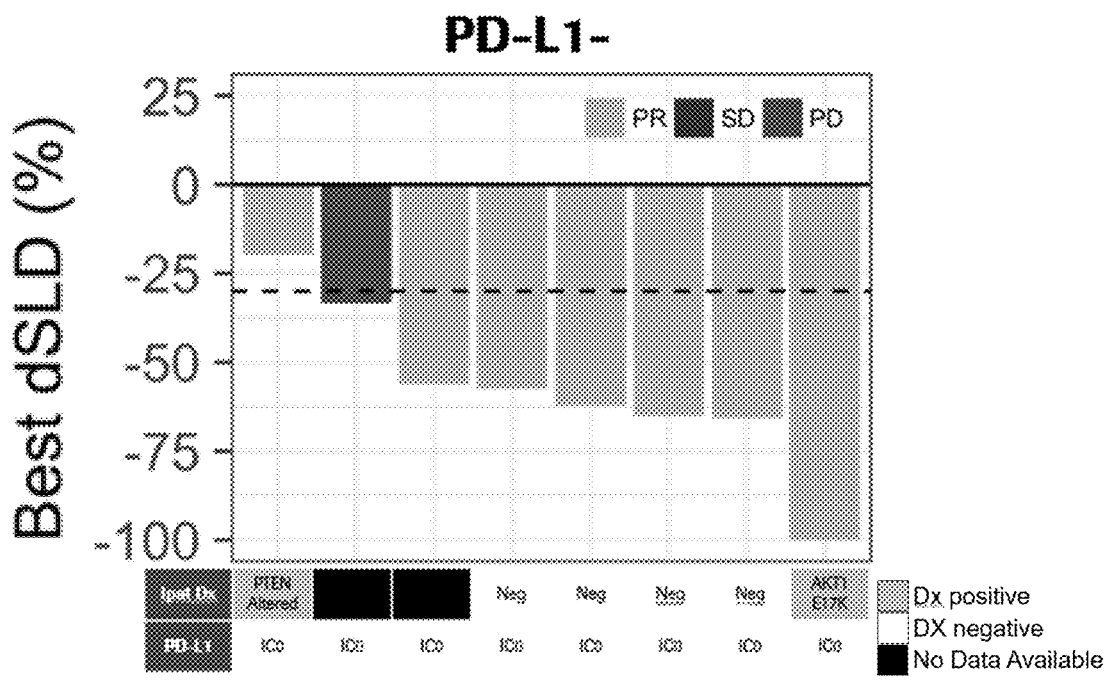
Figure 6:
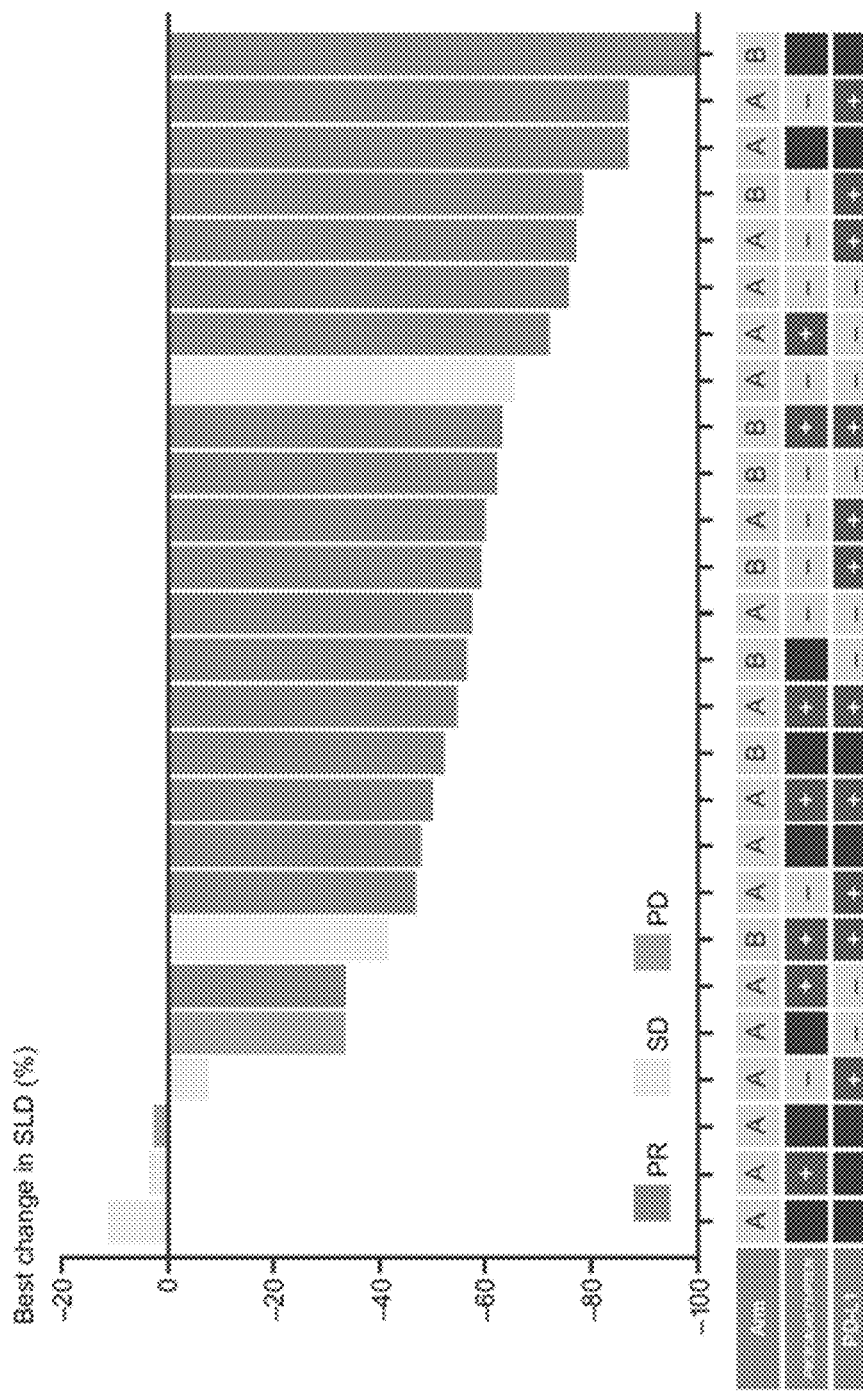
FIG. 6 depicts patient response annotated to indicate the diagnostic status for both PIK3CA/AKT1/PTEN-alterations and PD-L1 expression. SLD=sum of longest distances; PR=partial response; SD=stable disease; PD=progressive disease; ipat=ipatasertib.
Figure 7:
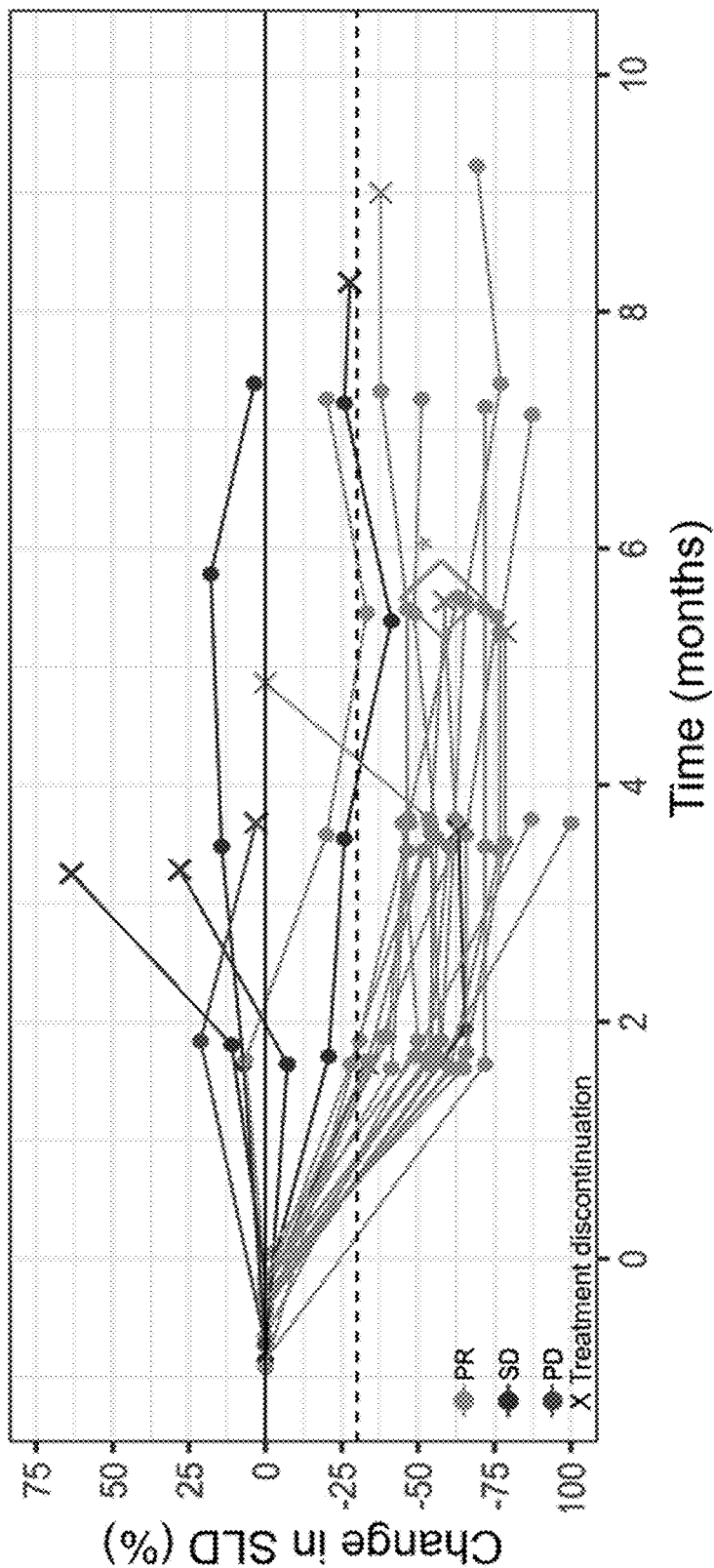
FIG. 7 depicts patient response and durability of response as function of change in SLD. PR=partial response; SD=stable disease; PD=progressive disease.

Patient response as a function of diagnostic confirmation for PTEN/PIK3CA/AKT alteration and PD-L1 are demonstrated in FIG. 4A/FIG. 4B, FIG. 5A/FIG. 5B, and FIG. 6. Patient response to treatment is reported in FIG. 6 and FIG. 7. Positive diagnostic status for treatment with ipatasertib in earlier trials provided evidence that a patient was likely to benefit from treatment. Similarly, positive diagnostic status for expression of PD-L1 indicated a greater likelihood of treatment benefit with atezolizumab treatment. In contrast, while the diagnostic status of the patients may be known and is useful, the benefit of treatment with the combination of ipatasertib/atezolizumab/taxane (e.g. paclitaxel or nab-paclitaxel) is independent of either diagnostic test. (See FIGS. 4A, 4B, 5A, 5B, and 6).

Responses were seen irrespective of PD-L1 status:
  82% (95% CI: 50-97%) response in 11 patients with PD-L1-positive tumors
  75% (95% CI: 35-95%) response in 8 patients with PD-L1-negative tumors.

Responses were seen irrespective of PIK3CA/AKT1/PTEN alteration status
  71% (95% CI: 34-95%) response in 7 patients with altered tumors
  82% (95% CI: 50-97%) response in 11 patients with non-altered tumors.

Figure 8:
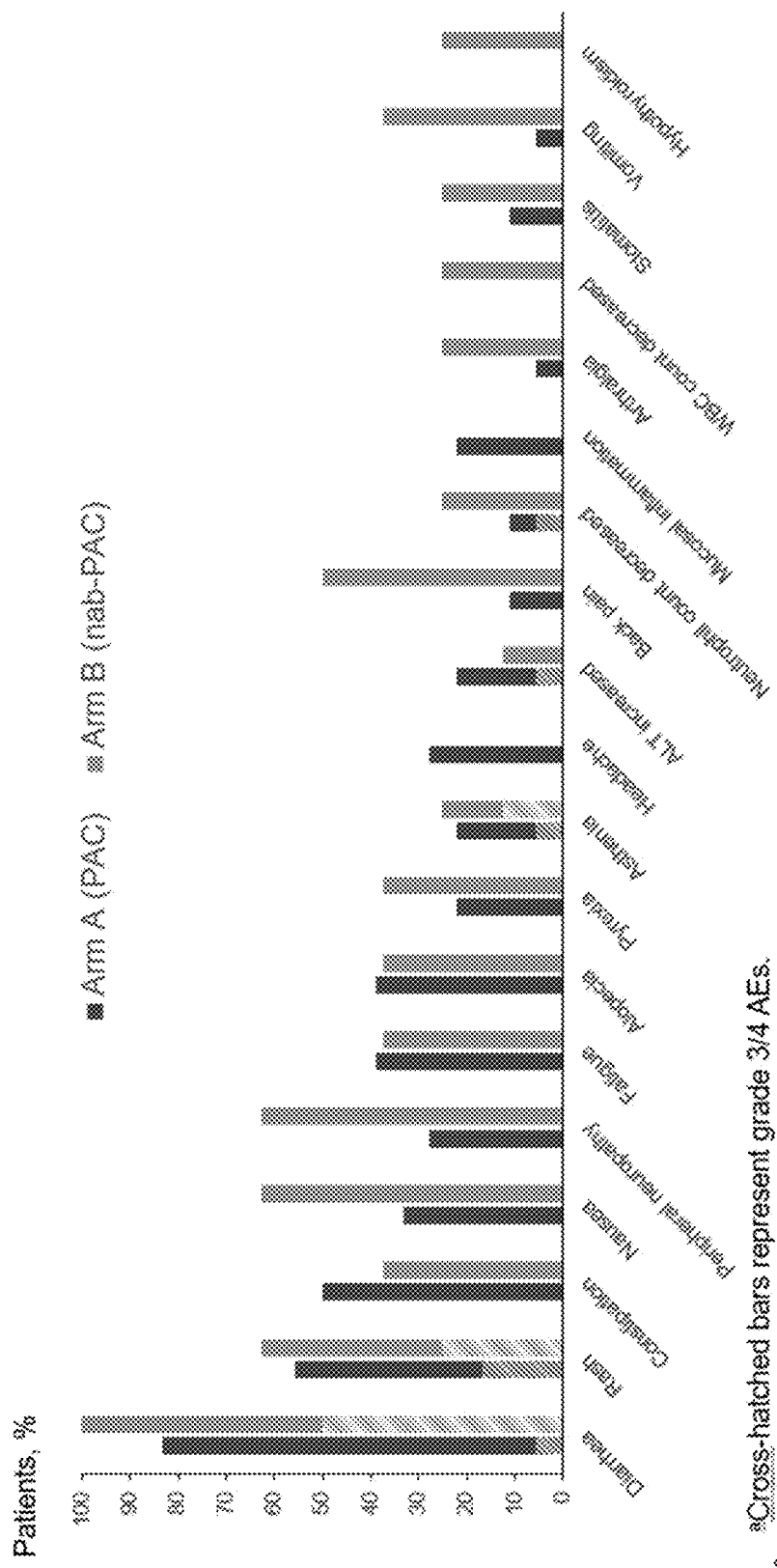
FIG. 8 depicts the most common adverse events (AEs) reported by patients in Arm A and Arm B described herein (any grade in >20% of total number of patients in both Arms).

Patients were further examined and questioned for the presence of adverse events (AEs). FIG. 8 shows the most common AEs of all grades. The most commonly reported AEs were diarrhea (all grades 88%; grade ≥3 19%) and rash (all grades 69%; grade ≥3 27%). There were no episodes of grade 4 rash. The first onset of rash was typically in cycle 1 and lasted a median duration of 15.5 days. There were cases of hyperglycemia reported. A summary of safety and adverse effects is reported in Table 4.

TABLE 4

Summary of AEs

| | Arm A (n = 18) | | Arm B (n = 8) | | |
|---|---|---|---|---|---|
| AE, n (%) | Safety run-in (n = 6) | Expansion (n = 12) | Safety run-in (n = 6) | Expansion (n = 2) | All patients (n = 26) |
| Any AE | 6 (100) | 12 (100) | 6 (100) | 2 (100) | 126 (100) |
| Grade 3 | 3 (50) | 5 (42) | 4 (67) | 1 (50) | 13 (50) |
| Grade 4 | 0 | 1 (8) | 0 | 0 | 1 (4) |
| Grade 5 | 0 | 0 | 0 | 0 | 0 |
| Serious AE | 4 (67) | 4 (33) | 4 (67) | 0 | 12 (46) |
| AE leading to treatment discontinuation | 2 (33) | 0 | 2 (33) | 1 (50) | 5 (19) |
| Ipatasertib | 0 | 0 | 0 | 1 (50)[a] | 1 (4) |
| Atezolizumab | 0 | 0 | 0 | 0 | 0 |
| PAC/nab-PAC | 2 (33)[b] | 0 | 2 (33)[c] | 0 | 4 (15) |

[a] Grade 3 diarrhea.
[b] Grade 2 peripheral neuropathy (n = 1) and grade 2 onychalgia (n = 1).
[c] Grade 2 peripheral neuropathy (n = 1) and grade 1 peripheral. neuropathy with grade 2 fatigue (n = 1).

Comparably, the most commonly reported AEs in the LOTUS Trial (treatment with ipatasertib/paclitaxel combination; n=61) were diarrhea (all grades 93.4%), nausea (all grades 49.2%) and fatigue (all grades 50.8%), and rash (all grades 16.4%).

Treatment with the combination therapy described herein was tolerable. Grade 23 adverse events (AEs) occurred in 14 patients (54%). The most common grade 23 AEs reported were diarrhea (19%) and rash (27%), both of which were manageable with standard therapies (e.g. loperamide or other antidiarrheal and antihistamines or steroids). Comparably, the LOTUS Trial presented a 23% rate of grade 23 diarrhea and a 1.6% rate of grade 23 rash.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating metastatic triple negative breast cancer (MTNBC) in a patient having MTNBC, the method comprising administering to the patient a combination therapy comprising:
    ipatasertib;
    (ii) atezolizumab; and
    (iii) paclitaxel or nab-paclitaxel,
wherein said combination therapy is administered over a 28-day cycle.

2. A method of treating locally advanced triple negative breast cancer (TNBC) in a patient having locally advanced TNBC, the method comprising administering to the patient a combination therapy comprising:
    (i) ipatasertib;
    (ii) atezolizumab; and
    (iii) paclitaxel or nab-paclitaxel,
wherein said combination therapy is administered over a 28-day cycle.

3. The method of claim 1 or 2, wherein ipatasertib is administered at an amount of 400 mg.

4. The method of claim 3, wherein the amount of ipatasertib administered to the patient is reduced to 300 mg or 200 mg.

5. The method of claim 3, wherein atezolizumab is administered at an amount of 840 mg by intravenous (IV) infusion.

6. The method of claim 3, wherein the combination therapy comprising administration of paclitaxel administered at an amount of 80 mg/m$^2$ by intravenous (IV) infusion.

7. The method of claim 6, wherein the amount of paclitaxel administered is reduced to 65 mg/m$^2$.

8. The method of claim 3, wherein the combination therapy is administered according to a dosing regimen comprising one 28-day cycle.

9. The method of claim 3, wherein the dosing regimen comprises a first administration period followed by 2-24 cycles of 28-day administration periods.

10. The method of claim 8, wherein cycle 1 of dosing regimen comprises:
    (i) administration of ipatasertib QD on day 1 through day 21;
    (ii) administration of atezolizumab on day 1 and day 15;
    (iii) administration of paclitaxel on day 1, day 8, and day 15; and
    (iv) a rest period of at least 7 days.

11. The method of claim 10, wherein the dosing regimen comprises at least one more cycle comprising:
    administration of ipatasertib QD on day 1 through day 21 of each of at least one more cycle;
    (ii) administration of atezolizumab on day 1 and day 15 of each of at least one more cycle;
    (iii) administration of paclitaxel on day 1, day 8, and day 15 of each of at least one more cycle; and
    (iv) a rest period of at least 7 days.

12. A method of treating metastatic triple negative breast cancer (MTNBC) or locally advanced TNBC in a patient having MTNBC or locally advanced TNBC, the method comprising administering to the patient a combination therapy comprising 400 mg ipatasertib, 840 mg atezolizumab, and 80 mg/m2 paclitaxel or 100 mg/m2 nab-paclitaxel according to a dosage regimen comprising at least one cycle, said cycle comprising administration of ipatasertib QD on days 1-21, administration of atezolizumab on days 1 and 15, and administration of paclitaxel or nab-paclitaxel on days 1, 8, and 15, followed by a 7-day rest period.

13. A method of inhibiting tumor growth or producing/increasing tumor regression in a patient having MTNBC or locally advanced TNBC, the method comprising administering to the patient a combination therapy according to the methods of any one of claim 8.

14. The method of any one of claim 8, wherein said patient experiences one or more adverse event selected from the group consisting of nausea, vomiting, diarrhea, stomatitis/mucosal inflammation, asthenia/fatigue, hyperglycemia, peripheral neuropathy, rash, neutropenia, IRRs, immune-related hepatitis, pneumonitis, colitis, pancreatitis, diabetes mellitus, hypothyroidism, hyperthyroidism, adrenal insufficiency, Guillain-Barré syndrome, hypophysitis, myasthenic syndrome or myasthenia gravis, meningoencephalitis, myocarditis, nephritis, alopecia, anemia, thrombocytopenia, cranial nerve palsies, myalgia, arthralgia, myocardial disorders, cardiac failure, angina, tachycardia, ventricular arrhythmia, cystoid macular edema, Stevens-Johnson syndrome/toxic epidermal necrolysis, sepsis, drug-induced liver injury, acute renal failure, hemolytic-uremic syndrome, erythema multiform, immune-mediated nephritis, and drug-induced lupus erythematous.

15. The method of claim 14, wherein the adverse event is rash.

16. The method of claim 15, wherein the patient is administered antihistamines or steroids.

17. The method of claim 16, wherein dosing regimen is not altered.

18. The method of claim 17, wherein the same amount of each agent and/or the timing of administration of the agents is not altered.

19. The method of claim 2, wherein said patient has TNBC determined to have a phosphatase and tensin homolog (PTEN) mutation, loss of PTEN expression, a phosphatidylinositol-4,5-bisphosphate 3-kinase catalytic subunit alpha (PIK3CA) mutation, a protein kinase B alpha (AKT1) mutation, or a combination thereof.

20. The method of claim 2, wherein the patient does not have Type I or Type II diabetes mellitus requiring insulin.

21. The method of claim 2, wherein the patient does not have lung disease selected from the group consisting of pneumonitis, interstitial lung disease, idiopathic pulmonary fibrosis, cystic fibrosis, Aspergillosis, and active tuberculosis.

22. The method of claim 2, wherein the patient does not have an autoimmune disease or an immune deficiency selected from the group consisting of myasthenia gravis, myositis, autoimmune hepatitis, systemic lupus erythematosus, rheumatoid arthritis, inflammatory bowel disease, antiphospholipid antibody syndrome, Wegener granulomatosis, Sjögren's syndrome, Guillain-Barré syndrome, and multiple sclerosis.

23. The method of claim 2, wherein the patient has not received allogeneic stem cell treatment.

24. The method of claim 2, wherein the patient has not received a prior solid organ transplantation.

25. The method of claim 2, wherein the patient has not taken a systemic immunosuppressive medication selected from the group consisting of corticosteroids, cyclophosphamide, azathioprine, methotrexate, thalidomide, and anti-tumor necrosis factor alpha agents within 2 weeks prior to administration of the combination therapy.

26. The method of claim 2, wherein the 28-day cycle is repeated until disease progression or unacceptable toxicity develops.

* * * * *